United States Patent
Chee et al.

(10) Patent No.: US 8,460,865 B2
(45) Date of Patent: *Jun. 11, 2013

(54) MULTIPLEX DECODING OF ARRAY SENSORS WITH MICROSPHERES

(75) Inventors: Mark S. Chee, Del Mar, CA (US); John R. Stuelpnagel, Encinitas, CA (US); Anthony W. Czarnik, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 860 days.

This patent is subject to a terminal disclaimer.

(21) Appl. No.: 11/739,668

(22) Filed: Apr. 24, 2007

(65) Prior Publication Data

US 2007/0231824 A1    Oct. 4, 2007

Related U.S. Application Data

(63) Continuation of application No. 10/187,321, filed on Jun. 28, 2002, now Pat. No. 7,226,734, and a continuation-in-part of application No. 09/344,526, filed on Jun. 24, 1999, now Pat. No. 7,060,431, which is a continuation-in-part of application No. 09/189,543, filed on Nov. 10, 1998, now abandoned, said application No. 11/739,668 is a continuation of application No. 11/285,722, filed on Nov. 22, 2005, now Pat. No. 7,455,971, which is a continuation-in-part of application No. 09/748,706, filed on Dec. 22, 2000, now Pat. No. 7,033,754, and a continuation-in-part of application No. 09/344,526, which is a continuation-in-part of application No. 09/189,543.

(60) Provisional application No. 60/302,213, filed on Jun. 28, 2001, provisional application No. 60/090,473, filed on Jun. 24, 1998, provisional application No. 60/235,531, filed on Sep. 26, 2000, provisional application No. 60/172,106, filed on Dec. 23, 1999.

(51) Int. Cl.
*C12Q 1/68* (2006.01)
*C07H 21/02* (2006.01)
*C07H 21/04* (2006.01)

(52) U.S. Cl.
USPC .......................... 435/6.1; 536/23.1; 536/24.3

(58) Field of Classification Search
None
See application file for complete search history.

(56) References Cited

U.S. PATENT DOCUMENTS

| | | |
|---|---|---|
| 3,712,535 A | 1/1973 | Genese et al. |
| 3,748,975 A | 7/1973 | Tarabocchia |
| 4,125,314 A | 11/1978 | Haskell et al. |
| 4,200,110 A | 4/1980 | Peterson et al. |

(Continued)

FOREIGN PATENT DOCUMENTS

| | | |
|---|---|---|
| EP | 0269764 | 6/1988 |
| EP | 0392546 | 10/1990 |

(Continued)

OTHER PUBLICATIONS

Abel et al, "Fiber-Optic Evanescent Wave Biosensor for the Detection of Oligonucleotides," Anal. Chem. 68:2905-2912 (1996).

(Continued)

*Primary Examiner* — Teresa E Strzelecka
(74) *Attorney, Agent, or Firm* — Knobbe, Martens, Olson & Bear, LLP

(57) ABSTRACT

The invention relates to compositions and methods for multiplex decoding of microsphere array sensors.

23 Claims, 13 Drawing Sheets

U.S. PATENT DOCUMENTS

| | | |
|---|---|---|
| 4,224,198 A | 9/1980 | Rembaum et al. |
| 4,448,485 A | 5/1984 | Bergman et al. |
| 4,499,052 A | 2/1985 | Fulyler |
| 4,582,789 A | 4/1986 | Sheldon, III et al. |
| 4,682,895 A | 7/1987 | Costello |
| 4,687,732 A | 8/1987 | Ward et al. |
| 4,729,949 A | 3/1988 | Weinreb et al. |
| 4,772,540 A | 9/1988 | Deutsch et al. |
| 4,785,814 A | 11/1988 | Kane |
| 4,822,746 A | 4/1989 | Walt |
| 4,824,789 A | 4/1989 | Yafuso et al. |
| 4,842,783 A | 6/1989 | Blaylock |
| 4,868,130 A | 9/1989 | Hargreaves |
| 4,876,187 A | 10/1989 | Duck et al. |
| 4,879,097 A | 11/1989 | Whitehead et al. |
| 4,894,343 A | 1/1990 | Tanaka et al. |
| 4,895,805 A | 1/1990 | Sato et al. |
| 4,981,783 A | 1/1991 | Augenlicht |
| 4,999,306 A | 3/1991 | Yafuso et al. |
| 5,002,867 A | 3/1991 | Macevicz |
| 5,015,843 A | 5/1991 | Seitz et al. |
| 5,019,350 A | 5/1991 | Rhum et al. |
| 5,026,599 A | 6/1991 | Koskenmaki |
| 5,028,545 A | 7/1991 | Soini |
| 5,061,336 A | 10/1991 | Soane |
| 5,071,531 A | 12/1991 | Soane |
| 5,105,305 A | 4/1992 | Betzig et al. |
| 5,110,745 A | 5/1992 | Kricka et al. |
| 5,114,864 A | 5/1992 | Walt |
| 5,126,022 A | 6/1992 | Soane et al. |
| 5,132,242 A | 7/1992 | Cheung |
| 5,135,627 A | 8/1992 | Soane |
| 5,143,853 A | 9/1992 | Walt |
| 5,176,881 A | 1/1993 | Sepaniak et al. |
| 5,177,012 A | 1/1993 | Kim et al. |
| 5,185,178 A | 2/1993 | Koskenmaki |
| 5,185,243 A | 2/1993 | Ullman et al. |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,259,926 A | 11/1993 | Kuwabara et al. |
| 5,272,081 A | 12/1993 | Weinreb et al. |
| 5,296,375 A | 3/1994 | Kricka et al. |
| 5,298,741 A | 3/1994 | Walt et al. |
| 5,302,509 A | 4/1994 | Cheeseman |
| 5,304,487 A | 4/1994 | Wilding et al. |
| 5,308,771 A | 5/1994 | Zhou et al. |
| 5,310,674 A | 5/1994 | Weinreb et al. |
| 5,313,545 A | 5/1994 | Kuo et al. |
| 5,320,814 A | 6/1994 | Walt et al. |
| 5,326,691 A | 7/1994 | Hozier et al. |
| 5,342,737 A | 8/1994 | Georger, Jr. et al. |
| 5,357,590 A | 10/1994 | Auracher |
| 5,380,489 A | 1/1995 | Sutton et al. |
| 5,435,724 A | 7/1995 | Goodman et al. |
| 5,462,700 A | 10/1995 | Beeson et al. |
| 5,474,895 A | 12/1995 | Ishii et al. |
| 5,481,629 A | 1/1996 | Tabuchi |
| 5,481,633 A | 1/1996 | Mayer |
| 5,486,335 A | 1/1996 | Wilding et al. |
| 5,494,798 A | 2/1996 | Gerdt et al. |
| 5,494,810 A | 2/1996 | Barany et al. |
| 5,496,997 A | 3/1996 | Pope |
| 5,498,392 A | 3/1996 | Wilding et al. |
| 5,506,141 A | 4/1996 | Weinreb et al. |
| 5,512,131 A | 4/1996 | Kumar et al. |
| 5,512,490 A | 4/1996 | Walt et al. |
| 5,516,635 A | 5/1996 | Ekins et al. |
| 5,518,863 A | 5/1996 | Pawluczyk |
| 5,518,883 A | 5/1996 | Soini |
| 5,541,311 A | 7/1996 | Dahlbert et al. |
| 5,545,531 A | 8/1996 | Rava et al. |
| 5,554,516 A | 9/1996 | Kacian et al. |
| 5,565,324 A | 10/1996 | Still et al. |
| 5,573,909 A | 11/1996 | Singer et al. |
| 5,575,849 A | 11/1996 | Honda et al. |
| 5,585,069 A | 12/1996 | Zanzucchi et al. |
| 5,587,128 A | 12/1996 | Wilding et al. |
| 5,589,351 A | 12/1996 | Harootunian |
| 5,593,838 A | 1/1997 | Zanzucchi et al. |
| 5,595,915 A | 1/1997 | Geysen |
| 5,603,351 A | 2/1997 | Cherukuri et al. |
| 5,604,097 A | 2/1997 | Brenner |
| 5,610,287 A | 3/1997 | Nikiforov et al. |
| 5,631,170 A | 5/1997 | Attridge |
| 5,631,337 A | 5/1997 | Sassi et al. |
| 5,632,876 A | 5/1997 | Zanzucchi et al. |
| 5,632,957 A | 5/1997 | Heller et al. |
| 5,633,972 A | 5/1997 | Walt et al. |
| 5,635,358 A | 6/1997 | Wilding et al. |
| 5,637,469 A | 6/1997 | Wilding et al. |
| 5,639,603 A | 6/1997 | Dower et al. |
| 5,640,234 A | 6/1997 | Roth et al. |
| 5,643,738 A | 7/1997 | Zanzucchi et al. |
| 5,647,030 A | 7/1997 | Jorgenson et al. |
| 5,649,576 A | 7/1997 | Kirk |
| 5,656,241 A | 8/1997 | Seifert et al. |
| 5,660,988 A | 8/1997 | Duck et al. |
| 5,671,303 A | 9/1997 | Shieh et al. |
| 5,674,698 A | 10/1997 | Zarling et al. |
| 5,677,196 A | 10/1997 | Herron et al. |
| 5,679,524 A | 10/1997 | Nikiforov et al. |
| 5,679,773 A | 10/1997 | Holmes |
| 5,681,484 A | 10/1997 | Zanzucchi et al. |
| 5,690,894 A | 11/1997 | Pinkel et al. |
| 5,714,330 A | 2/1998 | Brenner et al. |
| 5,726,026 A | 3/1998 | Wilding et al. |
| 5,736,330 A | 4/1998 | Fulton |
| 5,747,169 A | 5/1998 | Fan et al. |
| 5,747,180 A | 5/1998 | Miller et al. |
| 5,750,015 A | 5/1998 | Soane et al. |
| 5,755,942 A | 5/1998 | Zanzucchi et al. |
| 5,763,175 A | 6/1998 | Brenner |
| 5,766,963 A | 6/1998 | Baldwin et al. |
| 5,770,029 A | 6/1998 | Nelson et al. |
| 5,770,157 A | 6/1998 | Cargill et al. |
| 5,772,905 A | 6/1998 | Chou |
| 5,780,231 A | 7/1998 | Brenner |
| 5,795,714 A | 8/1998 | Cantor et al. |
| 5,795,716 A | 8/1998 | Chee |
| 5,814,524 A | 9/1998 | Walt |
| 5,815,178 A | 9/1998 | Silverbrook |
| 5,830,711 A | 11/1998 | Barany et al. |
| 5,837,196 A | 11/1998 | Pinkel et al. |
| 5,840,256 A | 11/1998 | Demers et al. |
| 5,843,655 A | 12/1998 | McGall |
| 5,846,842 A | 12/1998 | Herron et al. |
| 5,849,215 A | 12/1998 | Gin et al. |
| 5,854,033 A | 12/1998 | Lizardi |
| 5,854,684 A | 12/1998 | Stabile et al. |
| 5,856,083 A | 1/1999 | Chelsky et al. |
| 5,858,051 A | 1/1999 | Komiyama et al. |
| 5,858,732 A | 1/1999 | Solomon et al. |
| 5,863,708 A | 1/1999 | Zanzucchi et al. |
| 5,863,722 A | 1/1999 | Brenner |
| 5,866,331 A | 2/1999 | Singer et al. |
| 5,874,219 A | 2/1999 | Rava et al. |
| 5,876,924 A | 3/1999 | Zhang et al. |
| 5,881,200 A | 3/1999 | Burt |
| 5,888,723 A | 3/1999 | Sutton et al. |
| 5,888,885 A | 3/1999 | Xie |
| 5,900,481 A | 5/1999 | Lough et al. |
| 5,922,617 A | 7/1999 | Wang et al. |
| 5,976,797 A | 11/1999 | Mitsuhashi |
| 5,981,180 A | 11/1999 | Chandler et al. |
| 5,985,353 A | 11/1999 | Lawton et al. |
| 5,990,479 A | 11/1999 | Weiss et al. |
| 6,008,892 A | 12/1999 | Kain et al. |
| 6,013,456 A | 1/2000 | Akhavan-Tafti |
| 6,023,540 A | 2/2000 | Walt et al. |
| 6,027,889 A | 2/2000 | Barany et al. |
| 6,037,186 A | 3/2000 | Stimpson |
| 6,039,894 A | 3/2000 | Sanjurjo et al. |
| 6,045,760 A | 4/2000 | Aizawa et al. |

| Patent | Date | Inventor |
|---|---|---|
| 6,048,515 A | 4/2000 | Kresse et al. |
| 6,048,616 A | 4/2000 | Gallagher et al. |
| 6,051,380 A | 4/2000 | Sosnowski et al. |
| 6,054,564 A | 4/2000 | Barany et al. |
| 6,060,240 A | 5/2000 | Kamb et al. |
| 6,060,743 A | 5/2000 | Sugiyama et al. |
| 6,071,748 A | 6/2000 | Modlin et al. |
| 6,074,754 A | 6/2000 | Jacobsen et al. |
| 6,083,763 A | 7/2000 | Balch |
| 6,087,114 A | 7/2000 | Rider |
| 6,090,549 A | 7/2000 | Mirzabekov et al. |
| 6,090,553 A | 7/2000 | Matson |
| 6,090,666 A | 7/2000 | Ueda et al. |
| 6,096,496 A | 8/2000 | Frankel |
| 6,100,973 A | 8/2000 | Lawandy |
| 6,110,678 A | 8/2000 | Weisburg et al. |
| 6,114,038 A | 9/2000 | Castro et al. |
| 6,121,075 A | 9/2000 | Yamashita |
| 6,129,896 A | 10/2000 | Noonan et al. |
| 6,139,626 A | 10/2000 | Norris et al. |
| 6,172,218 B1 | 1/2001 | Brenner |
| 6,197,515 B1 | 3/2001 | Bamdad et al. |
| 6,200,737 B1 | 3/2001 | Walt et al. |
| 6,207,392 B1 | 3/2001 | Weiss et al. |
| 6,210,910 B1 | 4/2001 | Walt et al. |
| 6,251,639 B1 | 6/2001 | Kurn |
| 6,261,782 B1 | 7/2001 | Lizardi et al. |
| 6,266,459 B1 | 7/2001 | Walt et al. |
| 6,268,147 B1 | 7/2001 | Beattie et al. |
| 6,268,148 B1 | 7/2001 | Barany et al. |
| 6,274,323 B1 | 8/2001 | Bruchez et al. |
| 6,280,935 B1 | 8/2001 | Macevicz |
| 6,284,456 B1 | 9/2001 | Jones et al. |
| 6,284,465 B1 | 9/2001 | Wolber |
| 6,285,807 B1 | 9/2001 | Walt et al. |
| 6,306,643 B1 | 10/2001 | Gentalen et al. |
| 6,327,410 B1 | 12/2001 | Walt et al. |
| 6,355,198 B1 | 3/2002 | Kim et al. |
| 6,355,431 B1 | 3/2002 | Chee et al. |
| 6,361,718 B1 | 3/2002 | Shinmo et al. |
| 6,375,870 B1 | 4/2002 | Visovsky et al. |
| 6,377,721 B1 | 4/2002 | Walt et al. |
| 6,396,995 B1 | 5/2002 | Stuelpnagel et al. |
| 6,406,845 B1 | 6/2002 | Walt et al. |
| 6,429,027 B1 | 8/2002 | Chee et al. |
| 6,482,593 B2 | 11/2002 | Walt et al. |
| 6,500,603 B1 | 12/2002 | Shioda |
| 6,517,995 B1 | 2/2003 | Jacobson et al. |
| 6,544,732 B1 | 4/2003 | Chee et al. |
| 6,620,584 B1 | 9/2003 | Chee et al. |
| 6,653,030 B2 | 11/2003 | Mei et al. |
| 6,660,192 B1 | 12/2003 | Kim et al. |
| 6,720,007 B2 | 4/2004 | Walt et al. |
| 6,748,975 B2 | 6/2004 | Hartshorne et al. |
| 6,813,077 B2 | 11/2004 | Borrelli et al. |
| 6,847,773 B2 | 1/2005 | Korenaga et al. |
| 6,858,394 B1 | 2/2005 | Chee et al. |
| 6,859,570 B2 | 2/2005 | Walt et al. |
| 6,887,792 B2 | 5/2005 | Perlov et al. |
| 6,890,741 B2 | 5/2005 | Fan et al. |
| 6,890,764 B2 | 5/2005 | Chee et al. |
| 6,998,274 B2 | 2/2006 | Chee et al. |
| 7,166,431 B2 | 1/2007 | Chee et al. |
| 2001/0029049 A1 | 10/2001 | Walt et al. |
| 2002/0001801 A1 | 1/2002 | Fan et al. |
| 2002/0006617 A1 | 1/2002 | Fan et al. |
| 2002/0051971 A1 | 5/2002 | Stuelpnagel et al. |
| 2002/0059716 A1 | 5/2002 | Kropp et al. |
| 2002/0064896 A1 | 5/2002 | Zhao et al. |
| 2002/0115002 A1 | 8/2002 | Bailey et al. |
| 2002/0122612 A1 | 9/2002 | Walt et al. |
| 2002/0132221 A1 | 9/2002 | Chee et al. |
| 2002/0132241 A1 | 9/2002 | Fan et al. |
| 2002/0150909 A1 | 10/2002 | Stuelpnagel et al. |
| 2002/0172716 A1 | 11/2002 | Walt et al. |
| 2002/0177141 A1 | 11/2002 | Chee et al. |
| 2002/0187515 A1 | 12/2002 | Chee et al. |
| 2003/0003490 A1 | 1/2003 | Fan et al. |
| 2003/0016897 A1 | 1/2003 | Walt et al. |
| 2003/0027126 A1 | 2/2003 | Walt et al. |
| 2003/0217804 A1 | 11/2003 | Guo et al. |
| 2004/0021237 A1 | 2/2004 | Shimizu et al. |
| 2004/0081416 A1 | 4/2004 | Akutsu et al. |
| 2004/0245660 A1 | 12/2004 | Ohtsu et al. |
| 2005/0008286 A1 | 1/2005 | Ahn et al. |

FOREIGN PATENT DOCUMENTS

| | | |
|---|---|---|
| EP | 0478319 | 4/1992 |
| EP | 0539888 | 5/1993 |
| EP | 0572157 | 12/1993 |
| EP | 0723146 | 7/1996 |
| EP | 0799897 | 8/1997 |
| EP | 1 099 964 A2 | 5/2001 |
| FR | 2741357 | 5/1997 |
| GB | 2294319 A | 4/1996 |
| GB | 2315130 | 1/1998 |
| GB | 2315131 | 1/1998 |
| JP | 56-122001 | 9/1981 |
| JP | 02-131202 | 5/1990 |
| JP | 01283412 | 9/1991 |
| JP | 10-090544 | 4/1998 |
| JP | 10-268185 | 10/1998 |
| JP | 2001-154049 | 6/2001 |
| JP | 2001-185752 | 7/2001 |
| JP | 2001-318257 | 11/2001 |
| JP | 2002-071993 | 3/2002 |
| JP | 2002-311273 | 10/2002 |
| WO | WO 89/11101 | 11/1989 |
| WO | WO 92/09300 | 6/1992 |
| WO | WO 93/02360 | 2/1993 |
| WO | WO 93/25563 | 12/1993 |
| WO | WO 94/02515 | 2/1994 |
| WO | WO 94/12863 | 6/1994 |
| WO | WO 95/16918 | 6/1995 |
| WO | WO 95/21271 | 8/1995 |
| WO | WO 95/33070 | 12/1995 |
| WO | WO 96/03212 | 2/1996 |
| WO | WO 96/04547 | 2/1996 |
| WO | WO 96/11878 | 4/1996 |
| WO | WO 96/15271 | 5/1996 |
| WO | WO 96/30392 | 10/1996 |
| WO | WO 96/36436 | 11/1996 |
| WO | WO 96/40901 | 12/1996 |
| WO | WO 97/12030 | 4/1997 |
| WO | WO 97/13870 | 4/1997 |
| WO | WO 97/14028 | 4/1997 |
| WO | WO 97/27315 | 7/1997 |
| WO | WO 97/31256 | 8/1997 |
| WO | WO 97/40385 | 10/1997 |
| WO | WO 97/45559 | 12/1997 |
| WO | WO 97/46704 | 12/1997 |
| WO | WO 98/04746 | 2/1998 |
| WO | WO 98/08092 | 2/1998 |
| WO | WO 98/13523 | 4/1998 |
| WO | WO 98/20019 A | 5/1998 |
| WO | WO 98/29736 | 7/1998 |
| WO | WO 98/31836 | 7/1998 |
| WO | WO 98/40726 | 9/1998 |
| WO | WO 98/46797 | 10/1998 |
| WO | WO 98/50782 | 11/1998 |
| WO | WO 98/53093 | 11/1998 |
| WO | WO 98/53300 | 11/1998 |
| WO | WO 99/00663 | 1/1999 |
| WO | WO 99/05320 | 2/1999 |
| WO | WO 99/09394 | 2/1999 |
| WO | WO 99/13004 | 3/1999 |
| WO | WO 99/18434 | 4/1999 |
| WO | WO 99/28505 | 6/1999 |
| WO | WO 99/34931 | 7/1999 |
| WO | WO 99/39001 | 8/1999 |
| WO | WO 99/53087 | 10/1999 |
| WO | WO 99/60170 | 11/1999 |
| WO | WO 99/64867 | 12/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/16101 | 3/2000 |

| | | |
|---|---|---|
| WO | WO 00/26411 | 5/2000 |
| WO | WO 00/34299 | 6/2000 |
| WO | WO 00/39587 | 7/2000 |
| WO | WO 00/47767 | 8/2000 |
| WO | WO 00/47996 | 8/2000 |
| WO | WO 00/48000 | 8/2000 |
| WO | WO 00/58516 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/12862 | 2/2001 |
| WO | WO 01/18524 | 3/2001 |
| WO | WO 01/41918 | 6/2001 |
| WO | WO 01/46675 | 6/2001 |
| WO | WO 01/57268 | 8/2001 |
| WO | WO 01/57269 | 8/2001 |
| WO | WO 01/59432 | 8/2001 |
| WO | WO 01/61043 | 8/2001 |
| WO | WO 02/00336 | 1/2002 |
| WO | WO 02/12897 | 2/2002 |
| WO | WO 02/16649 | 2/2002 |
| WO | WO 02/21128 | 3/2002 |
| WO | WO 02/099982 | 12/2002 |
| WO | WO 02/101358 | 12/2002 |
| WO | WO 03/002979 | 12/2002 |
| WO | WO 03/006677 | 1/2003 |

OTHER PUBLICATIONS

Angel, S., "Optrodes: Chemically Selective Fiber-Optic Sensors," Spectroscopy, 2(4):38-47 (1987).
Anonymous, "Fluorescent Microspheres," Tech. Note 19, Bang Laboratories, (Fishers, In) Feb. 1997.
Anonymous, "Microsphere Selection Guide," Bang Laboratories, (Fisher, In) Sep. 1998.
Baner et al., "Signal amplification of padlock probes by rolling circle replication," Nucleic Acids Research, 26(22):5073-5078 (1998).
Bangs, L.B., "Immunological Applications of Microspheres," The Latex Course, Bangs Laboratories (Carmel, IN) Apr. 1996.
Barnard et al., "Fiber-Optic Organic Vapor Sensor," Environ. Sci. Technol., 25(7):1307-1304 (1991).
Barnard et al., "A Fibre-Optic Chemical Sensor with Discrete Sensing Sites," Nature, 353:338-340 (Sep. 1991).
Ben-Dor, A., et al., "Universal DNA Tag Systems: A Combinatorial Design Scheme," J. Compu. Biol. 7(3/4):503-519 (2000).
Birindelli, S. et al., "Comments on Adaptation of the Cellscan Technique for the SCM Test in Breast Cancer," European J. Cancer 33(8):1333-1334 (1997).
Brenner, S., et al. Gene Expression Analysis by Massively Parallel Signature Sequencing (MPSS) on Microbead Arrays, Nature Biotechnology 18:630-634 (2000).
Bruchez et al., "Semiconductor Nanocrystals as Fluorescent Biological Labels," Science, 281:p. 2013, Sep. 25, 1998.
Carey, W.P. et al., "Chemical Piezoelectric Sensor and Sensor Array Characterization," Anal. Chem. 58(14):3077-3084 (1986).
Castano, J. et al., "Dynamic Monitoring and Quantification of Gene Expression in Single Living Cells: A Molecular Basis for Secretory Cell Heterogeneity," Mol. Endo. 10(5):599-605 (1996).
Chen et al., "A Microsphere-Based Assay for Multiplexed Single Nucleotide Polymorphism Analysis Using Single Base Chain Extension," Genome Research, 10(4):549-557 (2000).
Chiavaroli, C. et al., "Simultaneous Monitoring of Cytosolic Free Calcium and Exocytosis at the Single Cell Leve," J. Neuroendocrinology 3(3):253-260 (1991).
Clark, R. et al., "Electrochemical Analysis in Picoliter Microvials," Anal. Chem. 69:259-263 (1997).
Czarnik, "Illuminating the SNP Genomic Code," Modern Drug Discovery, 1(2):49-55 (1998).
Danielson et al., "A Combinatorial Approach to the Discovery and Optimization of Luminescent Materials," Nature, 389:944-948 (1997).
DeForest, W.S., "Photoresist Materials and Processes," McGraw-Hill Book Company, New York. 89101 (1975).

Deutsch, M. et al., "Apparatus for High Precision Repetitive Sequential Optical Measurement of Living Dells," Cytometry 16:214-226 (1994).
Deutsch, M. et al., "Lymphocyte Fluorescence Polarization Measurements with the Cellscan System: Application to the SCM Cancer Test," Cytometry 23:159-165 (1996).
Dickinson et al., "Generating Sensor Diversity Through Combinatorial Polymer Synthesis," Analytical Chemistry, 69(17):3413-3418 (1997).
DiMarco, G. et al., "Luminescent $Ru^{11}$-Polypyridine Complexes in Poly-2-Hydroxyethyllmetharcrylate Matrices as Oxygen Sensors," Adv. Mater., 7(5):(1995).
Drmanac, R. et al., "Prospects for a Miniaturized, Simplified and Frugal Human Genome Project," Scientia Yugoslavica, 16(1-2):97-107 (1990).
Drmanac, R. et al., "Sequencing by Hybridization (SBH) with Oligonucleotide Probes as an Integral Approach for the Analysis of Complex Genomes," International Journal of Genome Research, 1(1):59-79 (1992).
Drmanac, R. et al., "Sequencing by Hybridization," Automated DNA Sequencing and Analysis, ed. M. Adams, C. Fields and J. Venter. (1994).
Drmanac, R. et al., "Sequencing byOligonucleotide Hybridization: A Promising Framework in Decoding of the Genome Program," The First International Conference on Electrophoresis, Supercomputing and the Human Genome, Proceedings on Apr. 10-13, 1990 Conference at Florida State University. Ed. C. Cantor and H. Lim.
Egner, B.J., et al., "Tagging in Combinatorial Chemistry: The Use of Coloured and Fluorescent Beads." Chem. Commun. (1997).
Fan, J.B. et al., "Parallel Genotyping of Human SNPs Using Generic High-density Oligonucleotide Tag Arrays," Genome Research, 10:853-860 (2000).
Fathi, et al., "Synthesis and Properties of Combinatorial Libraries of Phosphoramidates," J. Org. Chem. Soc. 61(16):5600-5609 (1996).
Ferguson et al., "A Fiber-Optic DNA Biosensor Microarray for the Analysis of Gene Expression," Nature Biotechnology, 14:1681-1684 (1996).
Fodor, S. et al., "Light-Directed, Spatially Addressable Parallel Chemical Synthesis," Science, 251:767-773 (1991).
Freeman, T. et al., "Oxygen Probe Based on Tetrakis(alkylamino)ethylene Chemiluminescence," Anal. Chem., 53:98102 (1981).
Fuh et al., "Single Fibre Optic Fluorescence pH Probe," Analyst, 112:1159-1163 (1987).
Gauci, M. et al., "Observation of Single-Cell Fluorescence Spectra in Laser Flow Cytometry," Cytometry 25:388-393 (1996).
Gerry, N. P., et al. "Universal DNA Microarray Method for Multiplex Detection of Low Abundance Point Mutations," J. Mol. Biol. 292:251-262 (1999).
Grime, G.W., Non-Silver Photographic Processes, Proceedings of the Symposium on Non-Silver Photographic Processes Held at New College, Oxford, Sep. 1973. "Holographic Diffraction Gratings Recorded in Photoresist," p. 275-284 (1973).
Gunderson, K.L. , "Mutation Detection by Ligation to Complete $n$-mer DNA Arrays," Genome Research 8:1142-1153 (1998).
Gunderson, et al. "Decoding Randomly Ordered DNA Arrays," Genome Research (2004) vol. 14, pp. 870-877.
Hafeman, D. et al., "Light-Addressab le Potentiometric sensor for biochemical systems," Science, 240:1182-1185 (1988).
Healey et al., "Development of a Penicillin Biosensor Using a Single Optical Imaging Fiber," SPIE Proc. 2388:568-573 (1995).
Healey et al., "Fiberoptic DNA Sensor Array Capable of Detecting Point Mutations," Analytical Biochemistry, 251:270-279 (1997).
Healey et al., "Improved Fiber-Optic Chemical Sensor for Penicillin," Anal. Chem. 67(24):4471-4476 (1995).
Hirschfeld et al., "Laser-Fiber-Optic "Optrode" for Real Time In Vivo Blood Carbon Dioxide Level Monitoring," Journal of Lightwave Technology, LT-5(7):1027-1033 (1987).
Hirschhorn, J.N. et al., "SBE-TAGS: An Array-Based Method for Efficient Single-Nucleotide Polymorphism Genotyping." PNAS 97(22):12164-12169 (2000).
Hogan, B. et al., "Single-cell Analysis at the Level of a Single Human Erythrocyte," Trends in Analytical Chemistry 12(1):4-9 (1993).

Hsuih et al., Novel, ligation-dependent PCR assay for detection of Hepatitis C Virus in Serum,: J. of Clinical Microbiology, 34(3):501-507 (1996).

Huang, L. et al., "Exploring Single-cell Dynamics Using Chemically-modified Microelectrodes," Trends in Analytical Chemistry 14(4):158-164 (1995).

Hubert, C. et al., "Design of a Solvatochromic Polymer-Based Fiber Optics Chemical Sensor for Polar Solvent Detection," Adv. Mater., 7(11):914-917 (1995).

Iannone et al., "Multiplexed Single Nucleotide Polymorphism Genotyping by Oligonucleotide Ligation and Flow Cytometry," Cytometry, 39:131-140 (2000).

Illumina Inc. "Emerging," Windhover's In Vivo, The Business and Medicine Report, p. 1-2, (Sep. 1998).

Ince, C. et al., "A Micro-Perfusion Chamber for Single-Cell Fluorescence Measurements," Journal of Immunological Methods 128:227-234 (1990).

Jacobs, J. et al., "Combinatorial chemistry—applications of light-directed chemical synthesis," TIBTECH, 12:19-26 (1994).

Koop, A. et al., "Continuous Bioluminescent Monitoring of Cytoplasmic ATP in Single Isolated Rat Hepatocytes During Metaboli Poisoning," Biochem. J. 295:165-170 (1993).

Lam, K.S., "The 'One-Bead-One-Compound' Combinatorial Library Method." Chem. Rev. 97(2):411-448 (1997).

Levy, U. et al., "Direct Picture Transmission in a Single Optical Fiber with Holographic Filters," Optics Communications, 30(2)163-165 (1979).

Lin et al., "A porous silicon-based optical interferometric biosensor," Science, 278:840-843 (1997).

Lin, Z. et al., "Multiplex genotype determination at a large number of gene loci," Proc. Natl. Sci. USA, 93:2582-2587 (Mar. 1996).

Lippitsch, M. et al., "Fibre-Optic Oxygen Sensor with the Fluorescence Decay Time as the Information Carrier," Anal. Chem. Acta., 205:1-6 (1998).

Lizardi et al., "Mutation detection and single-molecule counting using isothermal rolling-circle amplification," Nature Genetics, 19:225-232 (Jul. 1998).

Lonergan, M.C., "Array-Based Vapor Sensing Using Chemically Sensitive, Polymer Composite Resistors," IEEE Aerospace Applications Conference Proceedings, 3(8):583-631 (1997).

Lubbers, D. et al., "Optical Fluorescence Sensors for Continuous Measurement of Chemical Concentrations in Biological Systems," Sens. Actuators, 4:641-654 (1983).

Lundstrum, I. el al., "Artificial 'olfactory' images from a chemical sensor using a light-impulse technique," Nature, 352:47-50 (1991).

Luong, J. et al., "Fluorescence Sensors for Monitoring Bioprocesses," Practical Fluoro, ed. G.G. Guilbault, $2^{nd}$ Ed., Marcel Dekker. 775-793 (New York 1990).

Lyamichev et al., "Polymorphism identification and quantitative detection of genomic DNA by invasive cleavage of oligonucleotide probes," Nature Biotechnology, 17:292-296 (1999).

Matthews, J. et al., "Analytical Strategies for the Use of DNA Probes," Analytical Biochemistry, 169:125 (1988).

McConnell, et al., The Cytosensor Microphysiometer: Biological Applications of Silicon Technology, Science 257:1906-1912 (Sep. 1992).

Metzker, M. et al., "Termination of DNA synthesis by novel 3'-modified-deoxyribonucleoside 5'-triphosphates," Nucleic Acids Research, 22(20):4259-4267 (1994).

Michael et al., "Fabrication of Micro- and Nanostructures Using Optical Imaging Fibers and Their Use as Chemical Sensors," Proc. $3^{rd}$ Intl. Symp., Microstructures and Microfabricated Systems, ed. P.J. Hesketh, et al., v. 97-5, Electrochem. Sock., 152-157 (Aug. 1997).

Michael et al., "Making Sensors out of Disarray: Optical Sensor Microarrays," Proc. SPIE, 3270:34-41 (1998).

Michael et al., "Randomly Ordered Addressable High-Density Optical Sensor Arrays," Anal. Chem. 70(7):1242-1248 (Apr. 1998).

Mignani et al., "In-Vivo Biomedical Monitoring by Fiber-Optic Systems," Journal of Lightwave Technology, 13(7):1396-1406 (1995).

Milanovich et al., "Clinical Measurements Using Fiber Optics and Optrodes," Novel Optical Fiber Techniques for Medical Application, SPIE, 494:1831 (1984).

Miyawaki, A. et al., "Fluorescent Indicators for $Ca^{2+}$ Based on Green Fluorescent Proteins and Calmodulin," Nature 388:882-887 (Aug. 1997).

Mrksich, M. et al., "Controlling Cell Attachment of Contoured Surfaces with Self-Assemble Monlayers of Alkanethiolates on Gold," Proc. Natl. Acad. Sci. USA 93:10775-10778 (Oct. 1996).

Munkholm, C. et al., "A Fiber-Optic Sensor for $CO_2$ Measurement," Talanta, 35(2):109112 (1988).

Munkholm, C. et al., "Polymer Modification of Fiber Optic Chemical Sensors as a Method of Enhancing Fluorescence Signal for pH Measurement," Anal. Chem., 58:1427-1430 (1986).

Normie, L. "System Uses Photonics for Early Tumor Detection," Biophotonics International 24-25 (Sep./Oct. 1996).

Owicki, J. et al., "Bioassays with a Microphysiometer," Nature 344:271-272 (Mar. 1990).

Owicki, J. et al., "The Light-Addressable Potentiometric Sensor: Principles and Biological Applications," Annu. Rev. Biophys, Biomol. Sruct. 23:87-113 (1994).

Owicki, J. et al., "Continuous Monitoring of Receptor-Mediated Changes in the Metabolic Rates of Living Cells," Proc. Natl. Acad. Sci. USA 87:407-411 (1990).

Pantano et al., "Ordered Nanowell Arrays," Chem. Mater., 8(12):2832-2835 (1996).

Pantano et al., "Analytical Applications of Optical Imaging Fibers," Anal. Chem., 67:481A-487A (1995).

Parce et al., "Biosensors for Directly Measuring Cell Affecting Agents," Ann. Biol. Clin. 48:639-641 (1990).

Parce, J. et al., "Detection of Cell-Affecting Agents with a Silicon Biosensor," Science 246:243-247 (Oct. 1989).

Park, M. et al., "Block Copolymer Lithography: Periodic Arrays of $\sim 10^{11}$ Holes in 1 Square Centimeter," Science 276:1401-1404 (May 1997).

Peterson et al., Fiber-Optic Sensors for Biomedical Applications, Science, 12:123-127 (1984).

Peterson, J. et al., "Fiber Optic pH Probe for Physiological Use," Anal. Chem., 52:864-869 (1980).

Piunno et al., "Fiber-Optic DNA Sensor for Fluorometric Nucleic Acid Determination," Anal. Chem., 67:2635-2643 (1995).

Plunkett, M. et al., "Combinatorial Chemistry and New Drugs," Scientific American, Apr. 1997, 69-73.

Pope, E. "Fiber Optic Chemical Microsensors Employing Optically Active Silica Microspheres," SPIE, 2388:245-256 (1995).

Rahmani, et al., "Adaptation of the Cellscan Technique for the SCM Test in Breast Cancer," Eurpoean J. Cancer 32A(10): 1758-1765 (1996).

Ronaghi et al., "A Sequencing Method Based on Real-Time Pyrophosphate," Science, 281:363-365 (1998).

Rosenzweig, Z. et al., Analytical properties of miniaturized oxygen and glucose fiber optic sensors,: Sensors and Actuators, B 35-36, 475-483 (1996).

Saari et al., "pH Sensor Based on Immobolized Fluoresceinamine," Anal. Chem., 54:821-823 (1982).

Schwab, S. et al., "Versatile, Efficient Raman Sampling with Fiber Optics," Anal. Chem., 56:2199-2204 (1984).

Seitz, W.R., "Chemical Sensors Based on Fiber Optics," Anal. Chem., 56(1):1634A (1984).

Seitz, W.R. et al., "Chemical Sensors Based on Immobilized Indicators and Fiber Optics," C.R.C. Critical Reviews in Analytical Chemistry, 19(2):135173 (1988).

Seradyn, Sera-Mag Streptavidin Magnetic Microparticles, Particle Technology, Nov. 1996, pp. 1-7.

Shear, J. et al., "Single Cells as biosensors for Chemical Separations," Science 267:74-77 (1995).

Shoemaker, D.D. et al., "Quantitative phenotypic analysis of yeast deletion mutants using a highly parallel molecular bar-coding strategy," Nature Genetics, 14:450-456 (1996).

Slides presented by Illumina at Cambridge Healthtech Institute's Implications of Human Genetic Variation—SNP's, Polymorphisms, Diseases & Treatment. Nov. 18-19, 1998, Waltham, Massachusetts.

Smith, L. et al., "Fluorescence detection in automated DNA sequence analysis," Nature, 321, 674-679 (1986).

Still, W.C. et al, "Discovery of Sequence-Selective Peptide Binding by Synthetic Receptors Using Encoded Combinatorial Libraries," Ac. Chem. Res. 29(3):155-163 (1996).

Strachan et al., "A Rapid General Method for the Identification of PCR Products Using a Fibre-Optic Biosensor and its Application to the Detection of Listeria," Letters in Applied Microbiology, 21:5-9 (1995).

Syvanen, Anne-Christine. "From gels to chips: "Minisequencing" Primer Extension for Analysis of Point Mutations and Single Nucleotide Polymorphisms," Human Mutation, 13:1-10 (1999).

Tong, W. et al., "Monitoring Single-cell Pharmacokinetics by Capillary Electrophoresis and Laser-induced native Fluorescence," J. Chromatography B. 689:321-325 (1997).

Venton, D. et al., "Screening combinatorial libraries," Chemometrics and Intelligent Laboratory Systems, NL, Elsevier Science Publishers, Amsterdam, 48(2):131-150 (1999).

Vergne, I. et al.,"Phagosomal pH Determination by Duel Fluorescence Flow Cytometry," Analytical Biochemistry, vol. 2554(1), pp. 127-132 (Jan. 1, 1998).

Walt, D. et al., "Design, Preparation, and Applications of Fiber-Optic Chemical Sensors for Continuous Monitoring," Fiber Optic Chemical Sensors, Chemical Sensors and Microinstrumentation, 252-272 (1989).

Walt, D., "Fiber Optic Imaging Sensors," Accounts of Chemical Research, 31(5):267-278 (1998).

Walt, D., "Fiber-Optic Sensors for Continuous Clinical Monitoring," Proc. IEEE, 80(6):903-911 (1992).

White, J. et al., "Rapid Analyte Recognition in a Device Based on Optical Sensors and the Olfactory System," Analytical Chemistry, 68(13): 2191-2201 (1996).

Wightman, R.M. et al., "Monitoring Catecholamines at Single Cells," Trends in Analytical Chemistry 12(4):154-158 (1995).

Wolfbeis, O. et al., "Fiber-Optic Fluorosensor for Oxygen and Carbon Dioxide," Anal. Chem., 60:2028-2030 (1998).

Wolfbeis, O., "Tiber Optical Fluorsensors in Analytical and Clinical Chemistry," Molecular Luminescence Spectroscopy, Methods and Applications (S.G. Schulman, editor), Wiley & Sons, New York, 129-280 (1988).

Wong, K. et al., "Simultaneous Monitoring of Glutathione and Major Proteins in Single Erythrocytes," Mikrochim. Ata. 120:321-327 (1995).

Xiang, X. et al., "A Combinatorial Approach to Materials Discovery," Science, 268:1738-1740 (1995).

Yeung, E.S., "Chemical Analysis of Single Human Erythrocytes," Acc. Chem. Res. 27:409-414 (1994).

Zare, R.N., "Making a Biosensor from a Cell and a Fluorescent Dye," Biophotonics International, 17 (Mar./Apr. 1995).

Zellers, E. et al., "Optimal Coating Selection for the Analysis of Organic Mixtures with Polymer-Coated Surface Acoustic Wave Sensor Arrays," Analytical Chemistry, 67(6):1092-1106 (1995).

Zhang, et la., "A Combinatorial Method for the Solid Phase Synthesis of Alpha-Amino Phosphates and Phosphonic Acids," TrtRahedron Letter, 37(31):5457-5460 (1996).

Zhujun, Z. et al., "A fluorescence Sensor for Quantifying pH in the Range for 6.5 to 8.5," Anal. Chem. Acta., 160:47-55 (1984).

Zurgil, N. et al., "Intracellular Fluorescence Polarization Measurements by the Cellscan System: Detection of Cellular Activity in Autoimmune Disorders," Isr. J. Med. Sci. 33:273-279 (1997).

Adleman, Lenoard M., "Molecular Computation of Solutions to Combinatorial Problems" *Science* (1994) 266: 1021-1024.

Burmeister, Margit and Hans Lehrach, "Long-range restriction map around the Duchenne muscular dystrophy gene" *Nature* (1986) 324: 582-585.

Poustka, et al., "Molecular Approaches to Mammalian Genetics" *Cold Spring Harb Symp Quant Biol* (1986) 51: 131-139.

Roweis, et al., "A Sticker Based Model for DNA Computation" *DIMACS* (1999) 44: 1-29.

Shelton, Charles P., "Coding for Error Detection and Correction" Carnegie Mellow University (1999), obtained from http://www.ece.cmu.edu/~koopman/des_s99/coding/ on Jan. 27, 2011.

Definition of "Parity Check" from http://www.thefreedictionary.com/parity+check, obtained on Sep. 15, 2009.

Letter dated Sep. 17, 2009, filed on behalf of Opponent regarding Notice of Opposition to European Patent EP 1240498.

Communication dated Sep. 20, 2009, from the European Patent Office to Proprietor regarding Notice of Opposition filed in European Patent EP 1240498.

Communication dated Oct. 27, 2009, from the European Patent Office to Proprietor informing them that no further Opposition has been filed in European Patent EP 1240498.

Communication dated Oct. 27, 2009, from the European Patent Office to Proprietor regarding Notice of Opposition filed in European Patent EP 1240498.

Letter dated Apr. 29, 2010, filed on behalf of Proprietor in response to the Notice of Opposition filed in European Patent EP 1240498.

Communication dated Dec. 12, 2010, from the European Patent Office regarding Facts and Submissions of the Notice of Opposition filed in European Patent EP 1240498.

Letter dated Jan. 28, 2011, filed on behalf of Proprietor in response to the Summons to Oral Proceedings issued in European Patent EP 1240498.

Letter dated Jan. 28, 2011, filed on behalf of Opponent in response to Preliminary Opinion and Summons to Oral Proceedings issued in European Patent EP 1240498.

Letter dated Nov. 17, 2009, filed on behalf of Opponent regarding Notice of Opposition to European Patent EP 1090293.

Communication dated Nov. 30, 2009, from the European Patent Office to Opponent regarding Deficiencies in the Notice of Opposition to European Patent EP 1090293.

Letter dated Dec. 9, 2009, filed on behalf of the Opponent in response to communication regarding Deficiencies in the Notice of Opposition to European Patent EP 1090293.

Communication dated Dec. 29, 2009, from the European Patent Office to the Proprietor regarding Notice of Opposition filed in European Patent EP 1090293.

Communication dated Dec. 29, 2009, from the European Patent Office to Proprietor informing them that no further Opposition has been filed in European Patent EP 1090293.

Letter dated Oct. 21, 2010, filed on behalf of Proprietor in response to the Notice of Opposition filed in European Patent EP 1090293.

Letter dated Jan. 28, 2011, filed on behalf of Proprietor in response to the Summons to Oral Proceedings issued in European Patent EP 1090293.

Letter dated Jan. 28, 2011, filed on behalf of Proprietor in response to the Summons to Oral Proceecings issued in European Patent EP 1090293.

Schena, Mark, *Microarray Biochip Technology*, Eaton Publishing, Natick, MA, 2000.

Decision rejecting the opposition, dated May 25, 2011, in connection with the Opposition of European Patent EP 1240498.

Minutes of the oral proceedings before the Opposition Division, dated Mar. 29, 2011, in connection with the Opposition of European Patent EP 1240498.

Minutes of the oral proceedings before the Opposition Division, dated Mar. 30, 2011, in connection with the Opposition of European Patent EP 1240498.

Letter from Opponent, dated Jul. 25, 2011, in connection with the Opposition of European Patent EP 1240498.

Notice of Appeal filed on behalf of Opponent, dated Jul. 27, 2011, in connection with the Opposition of European Patent EP 1240498.

Gunderson, et al, "Decoding Randomly Ordered DNA Arrays" *Genome Research* (2004) 14: 870-877.

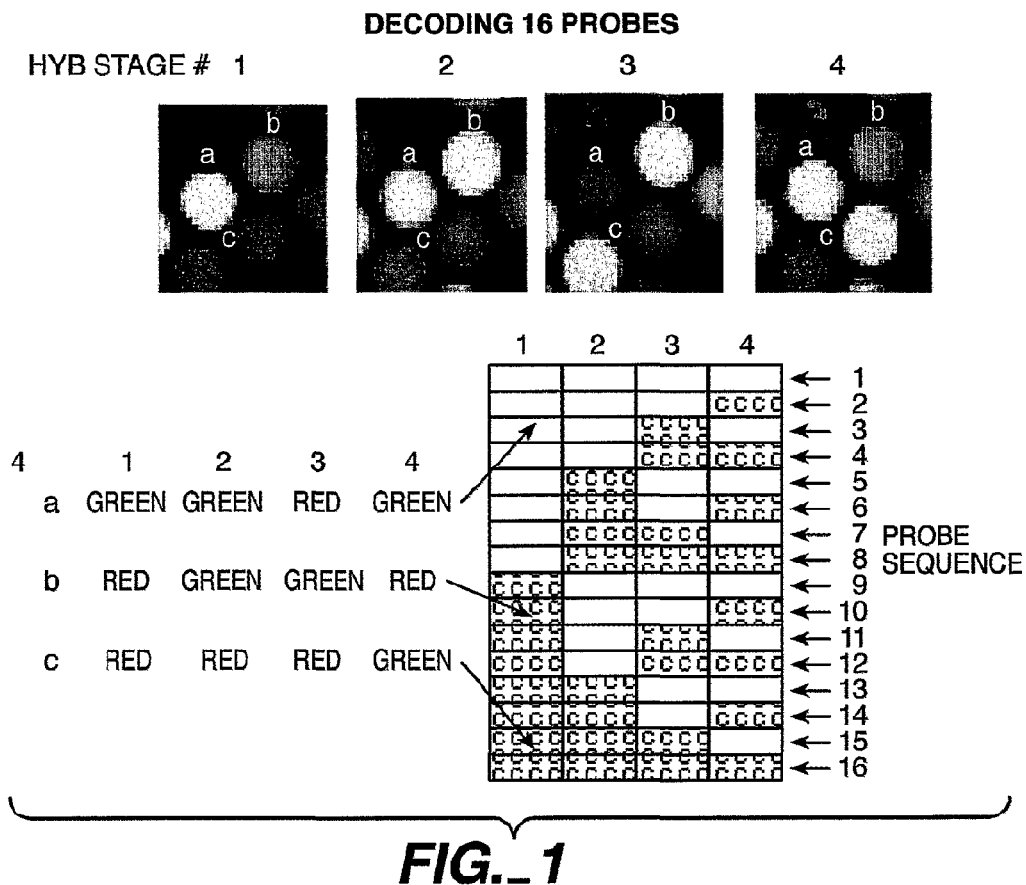
FIG._1
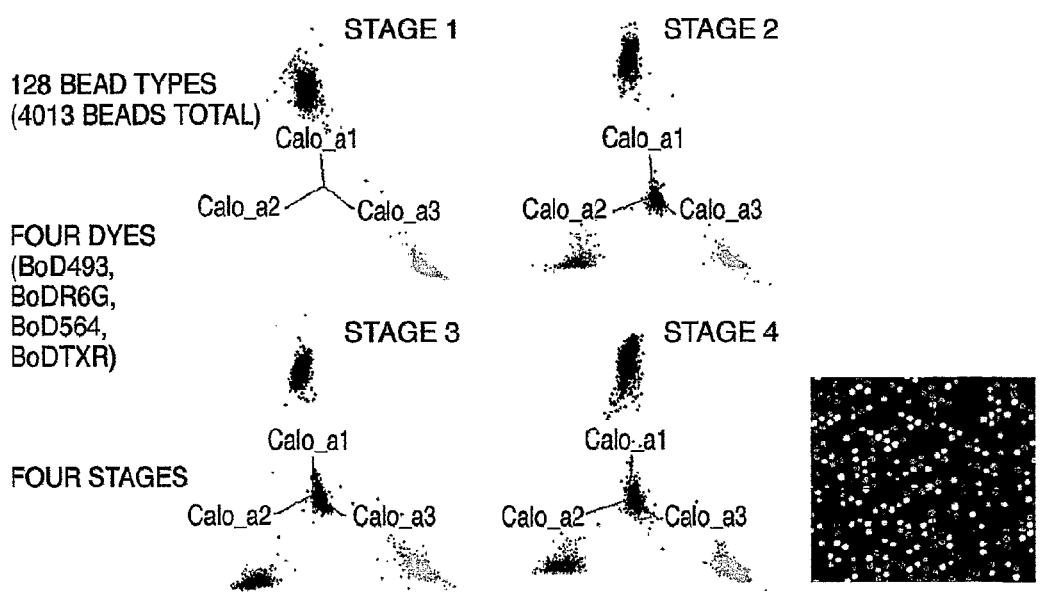
FIG._2

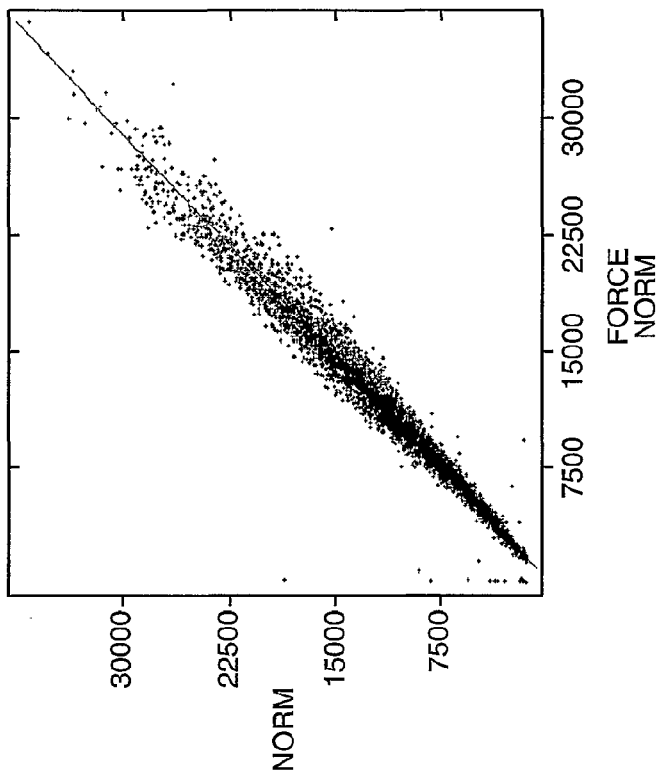
FIG._3B
FIG._3A

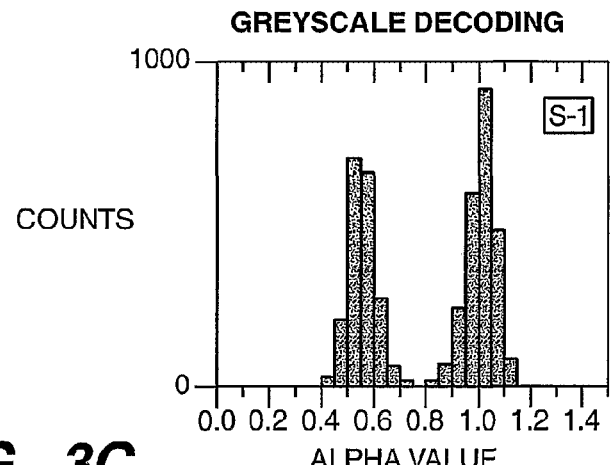
FIG._3C
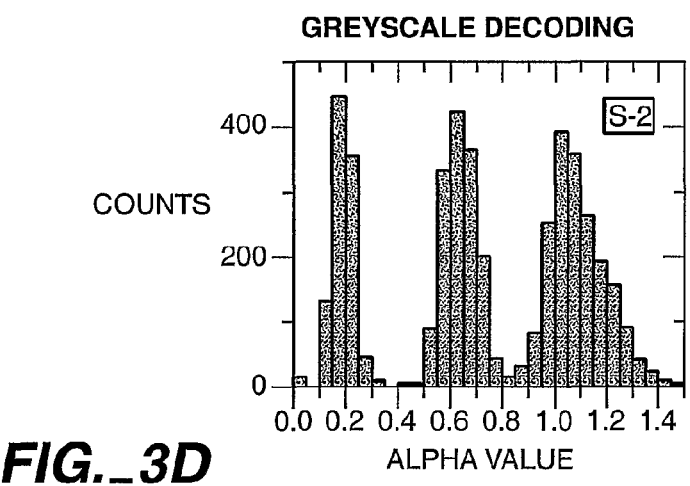
FIG._3D
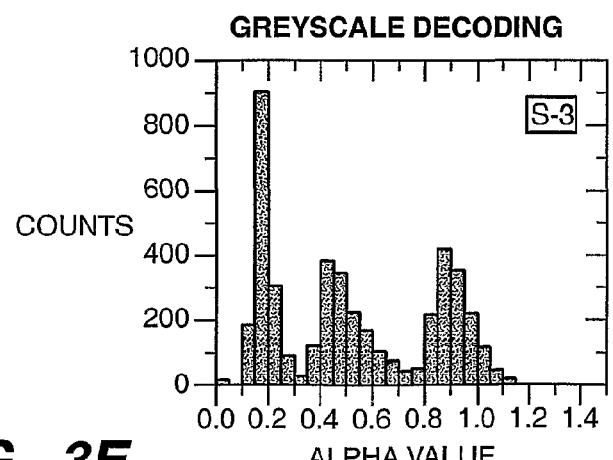
FIG._3E

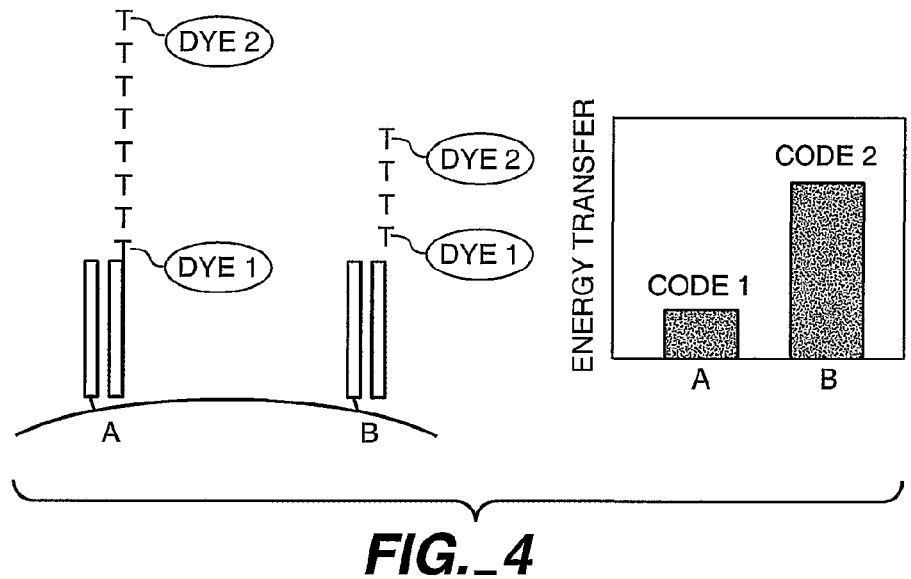
FIG._4
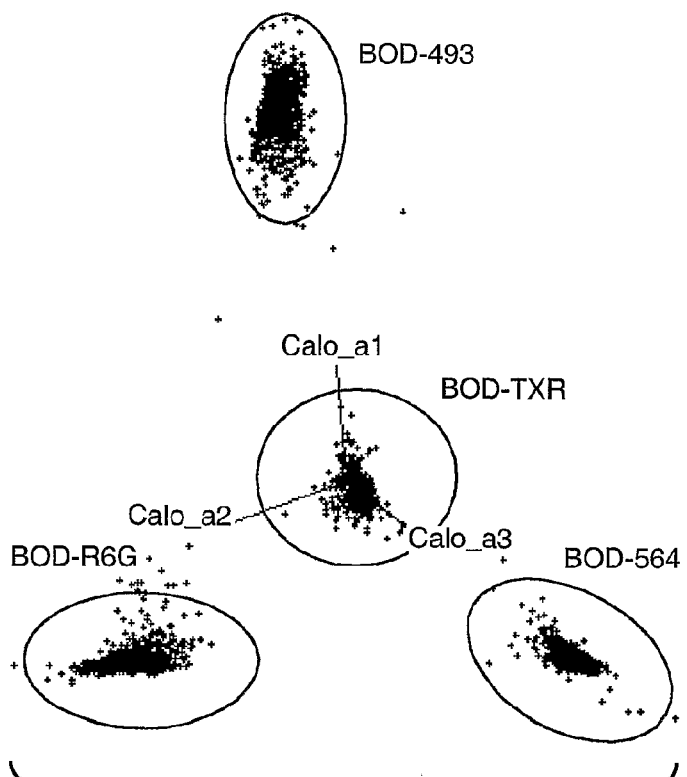
FIG._6

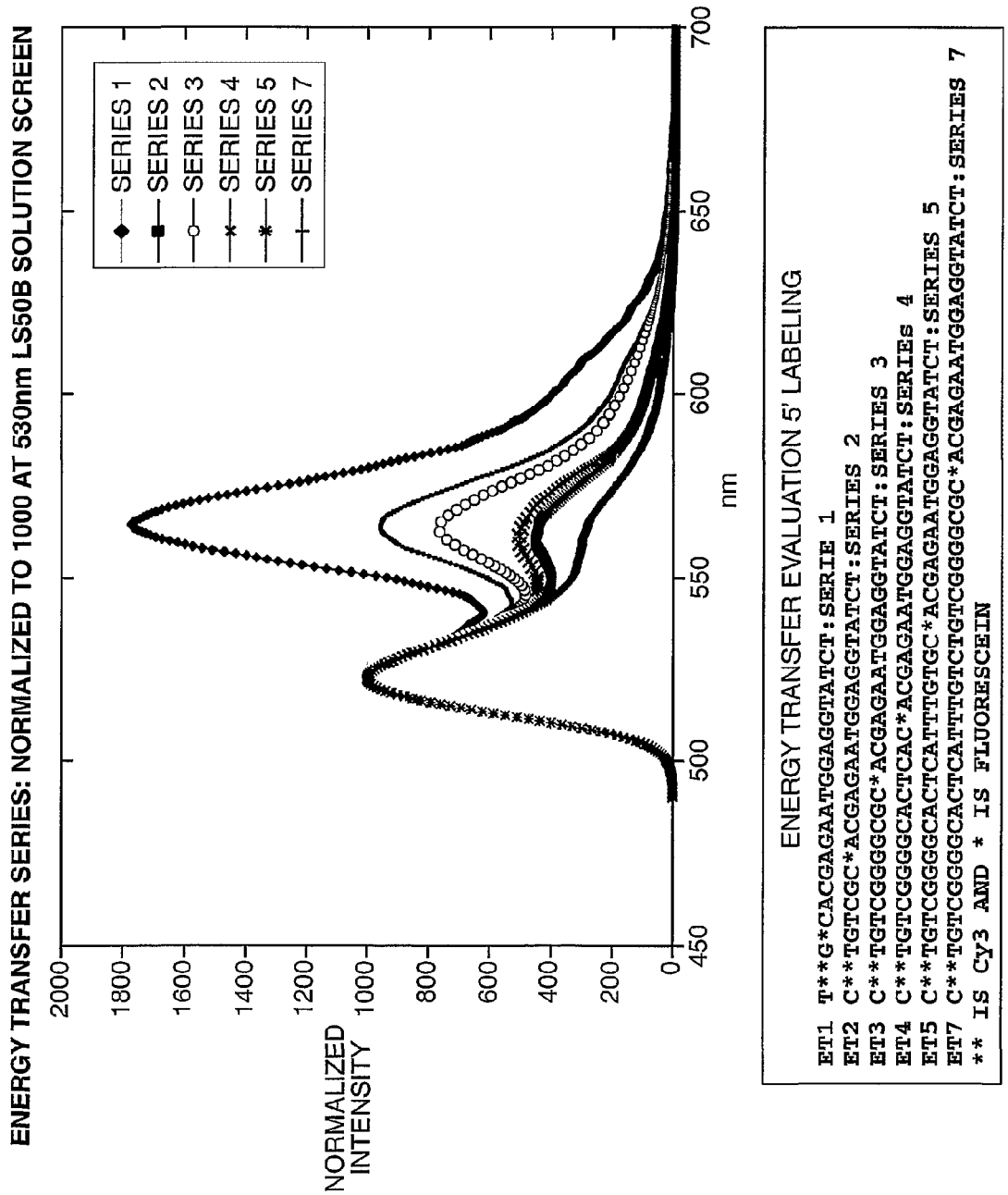
FIG._5

| BEAD | 1 "COLOR" DECODING | | | | CODE | PARITY |
|---|---|---|---|---|---|---|
| | STAGE 1 | STAGE 2 | STAGE 3 | STAGE 4 | | |
| 1 | 1 | 1 | 1 | 1 | 1111 | EVEN |
| | 1 | 1 | 1 | | 1110 | ODD |
| | 1 | 1 | | 1 | 1101 | ODD |
| 2 | 1 | 1 | | | 1100 | EVEN |
| | 1 | | 1 | 1 | 1011 | ODD |
| 3 | 1 | | 1 | | 1010 | EVEN |
| 4 | 1 | | | 1 | 1001 | EVEN |
| | 1 | | | | 1000 | ODD |
| | | 1 | 1 | 1 | 0111 | ODD |
| 5 | | 1 | 1 | | 0110 | EVEN |
| 6 | | 1 | | 1 | 0101 | EVEN |
| | | 1 | | | 0100 | ODD |
| 7 | | | 1 | 1 | 0011 | EVEN |
| | | | 1 | | 0010 | ODD |
| | | | | 1 | 0001 | ODD |
| 8 | | | | | 0000 | EVEN |

1001 DIGIT SUM = 2, EVEN PARITY
↓
1011 DIGIT SUM = 3, ODD PARITY

FIG._7

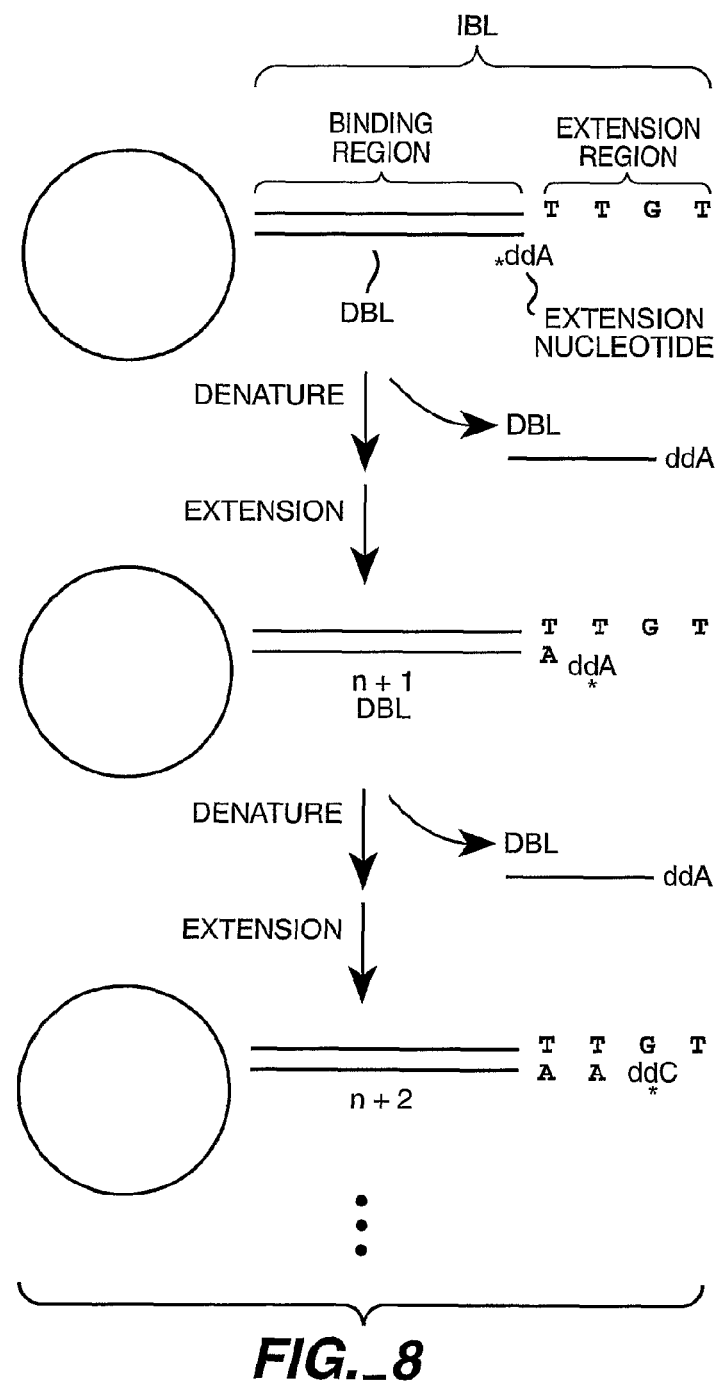
FIG._8

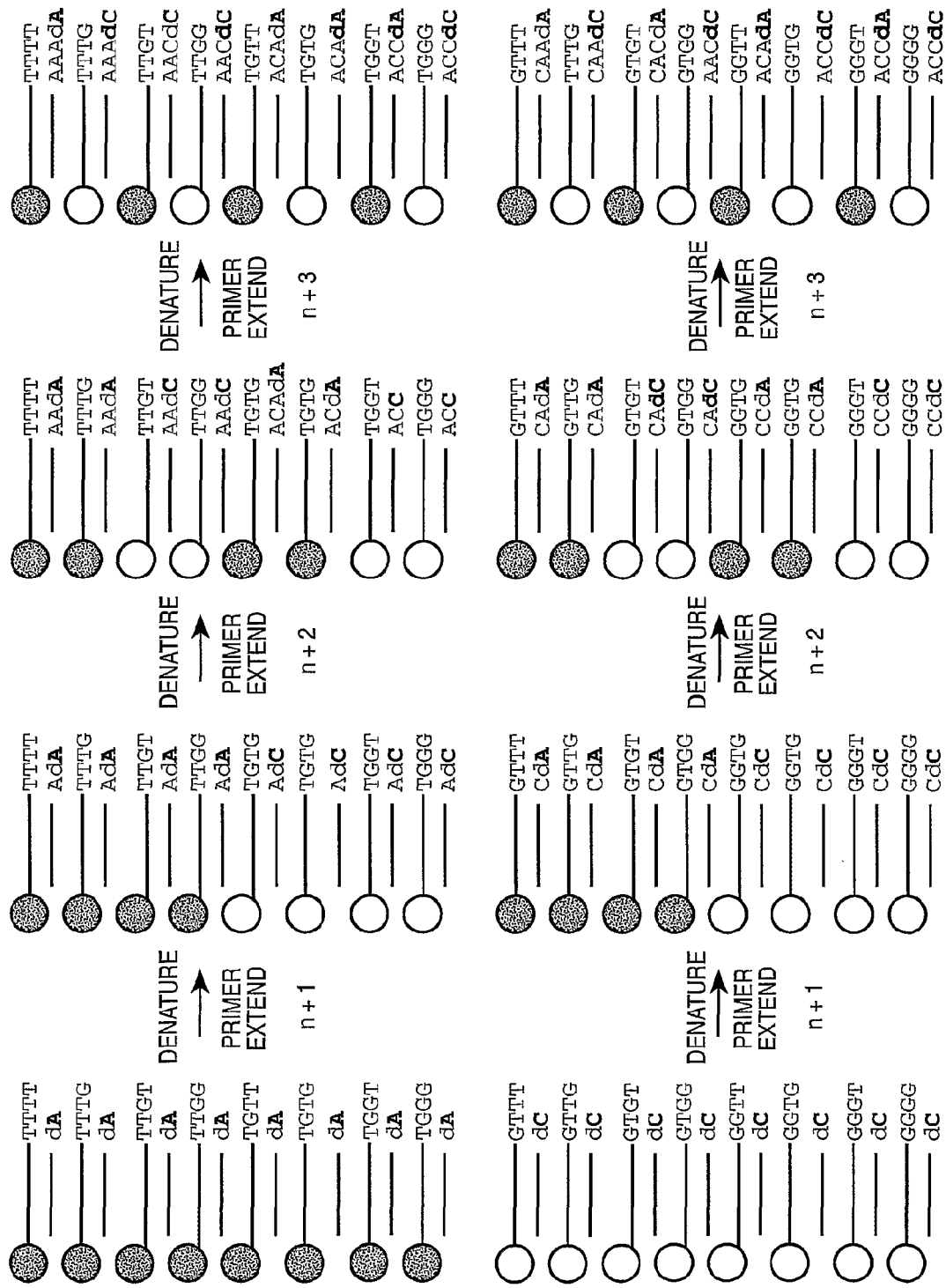
FIG._9

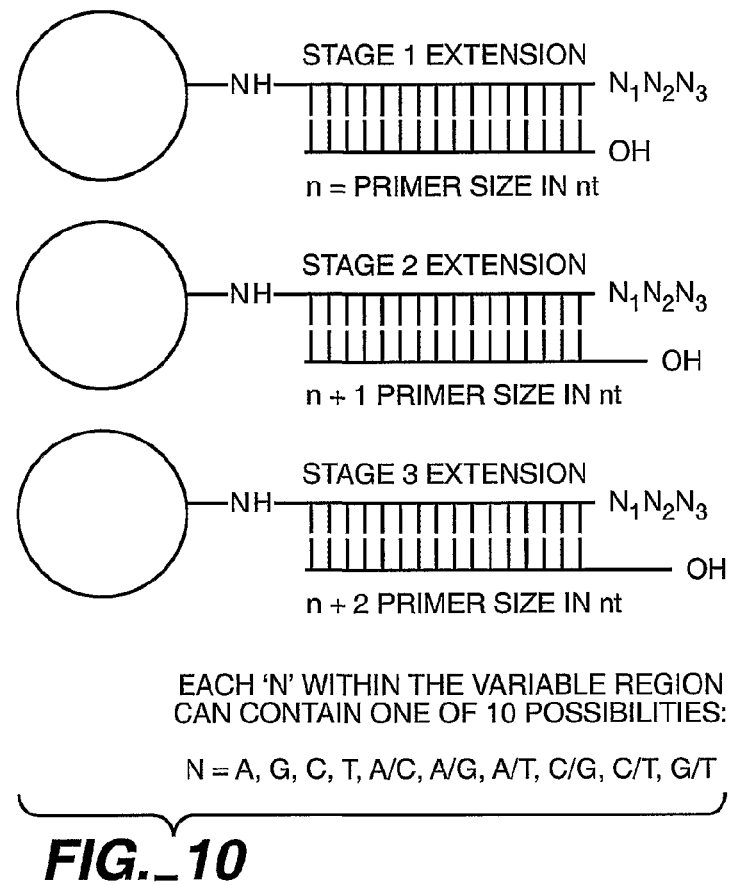
FIG._10
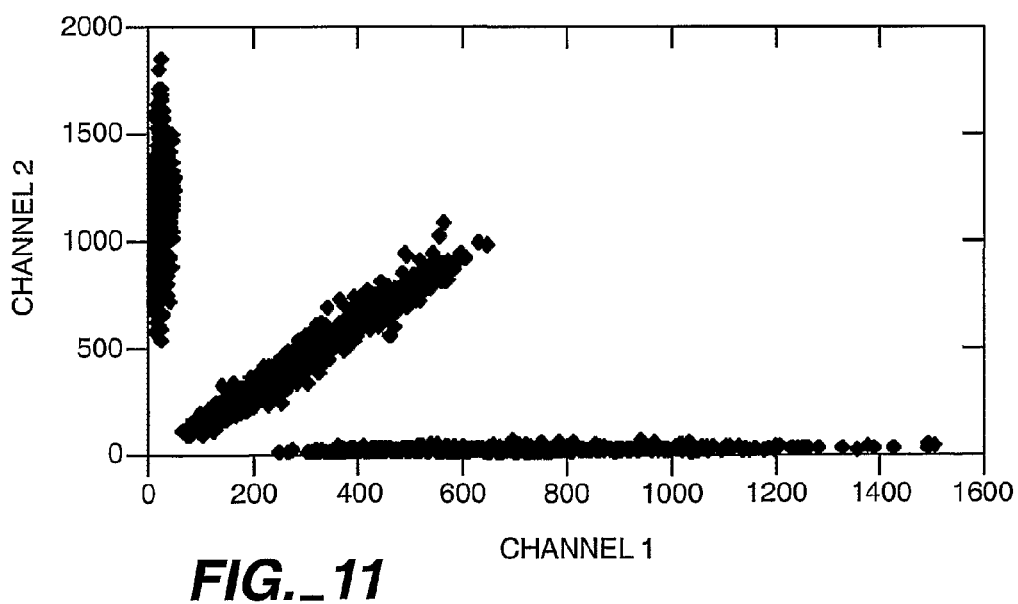
FIG._11

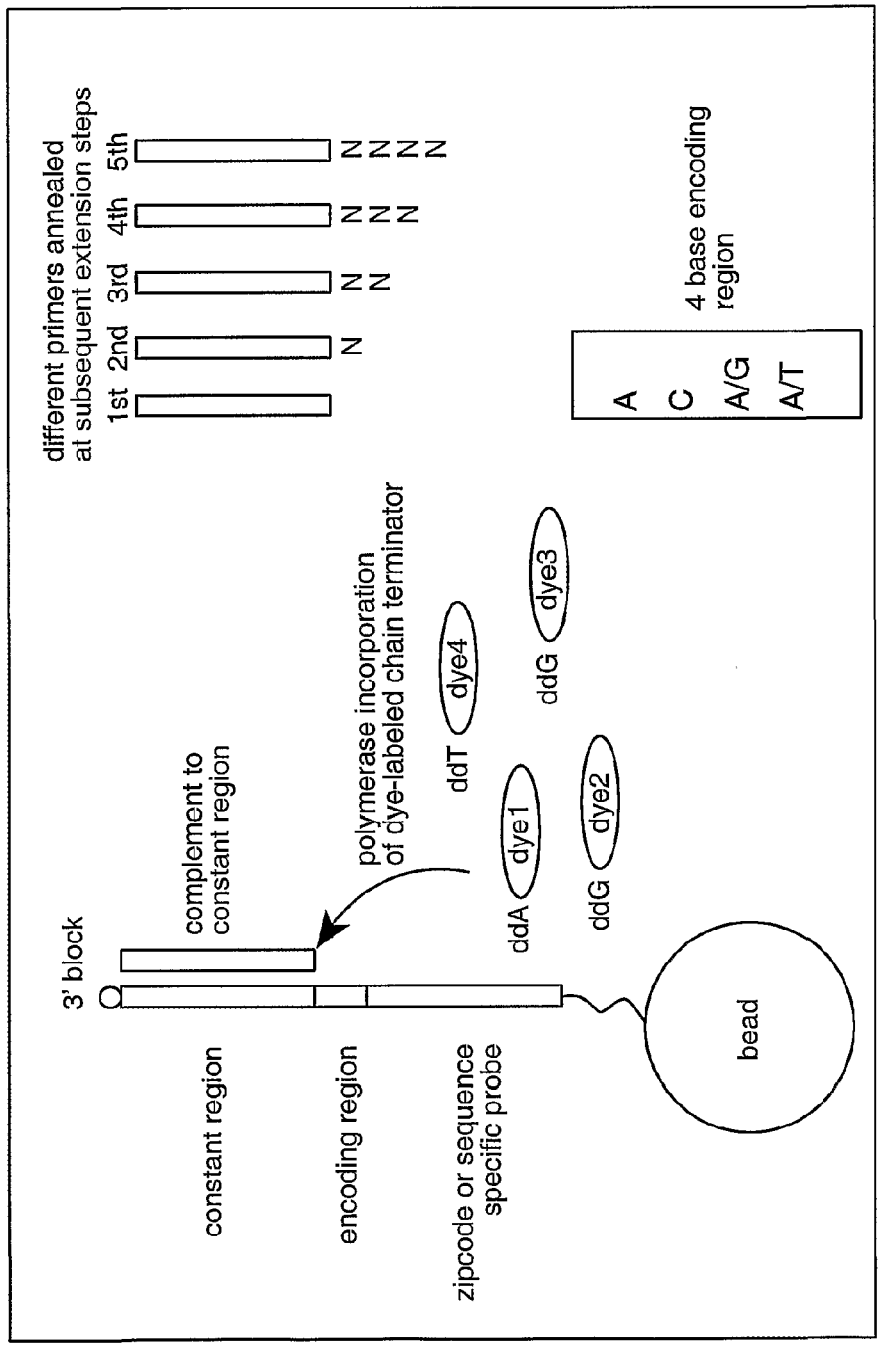
FIG._12

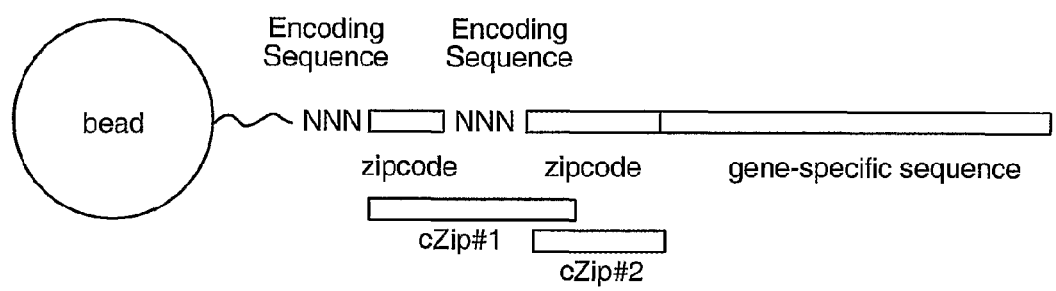
FIG._13
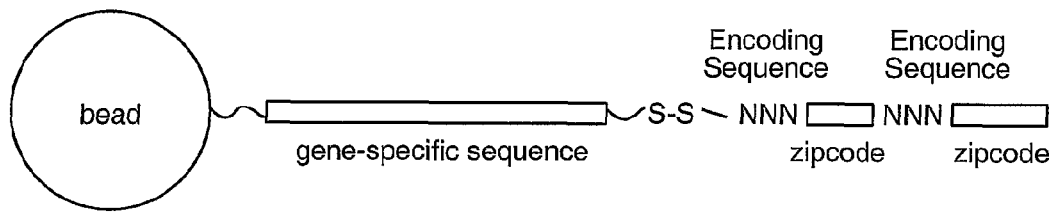
FIG._14

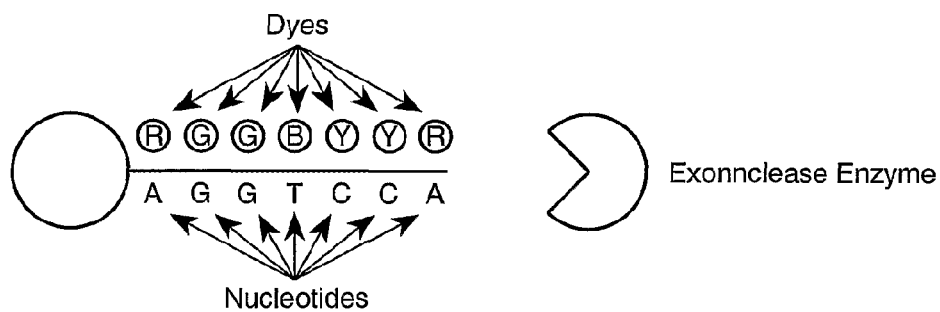
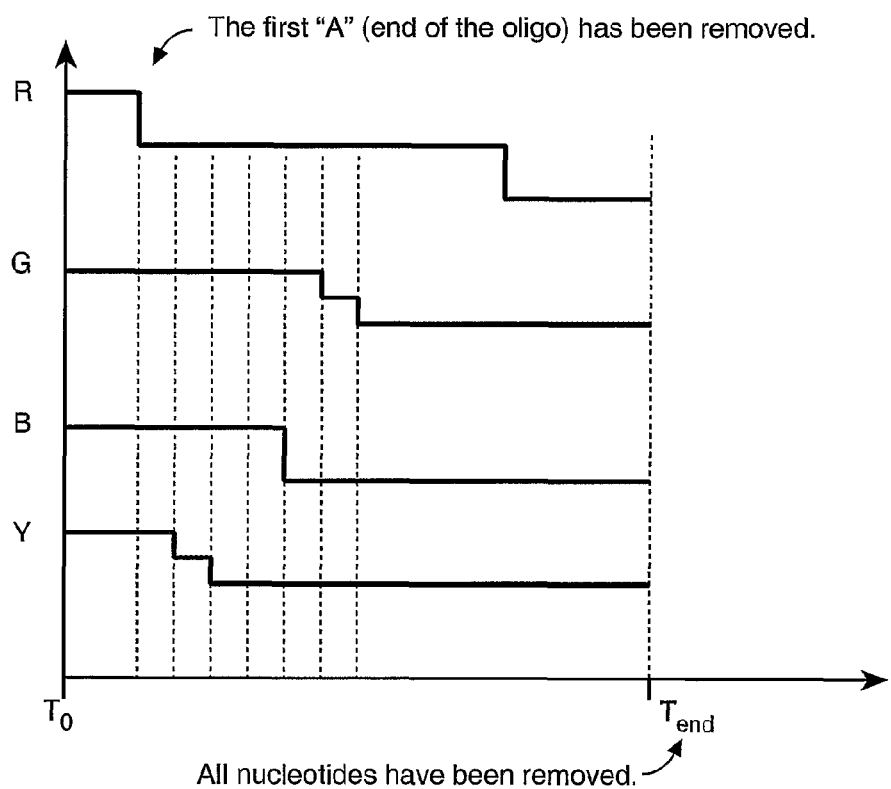
FIG._15

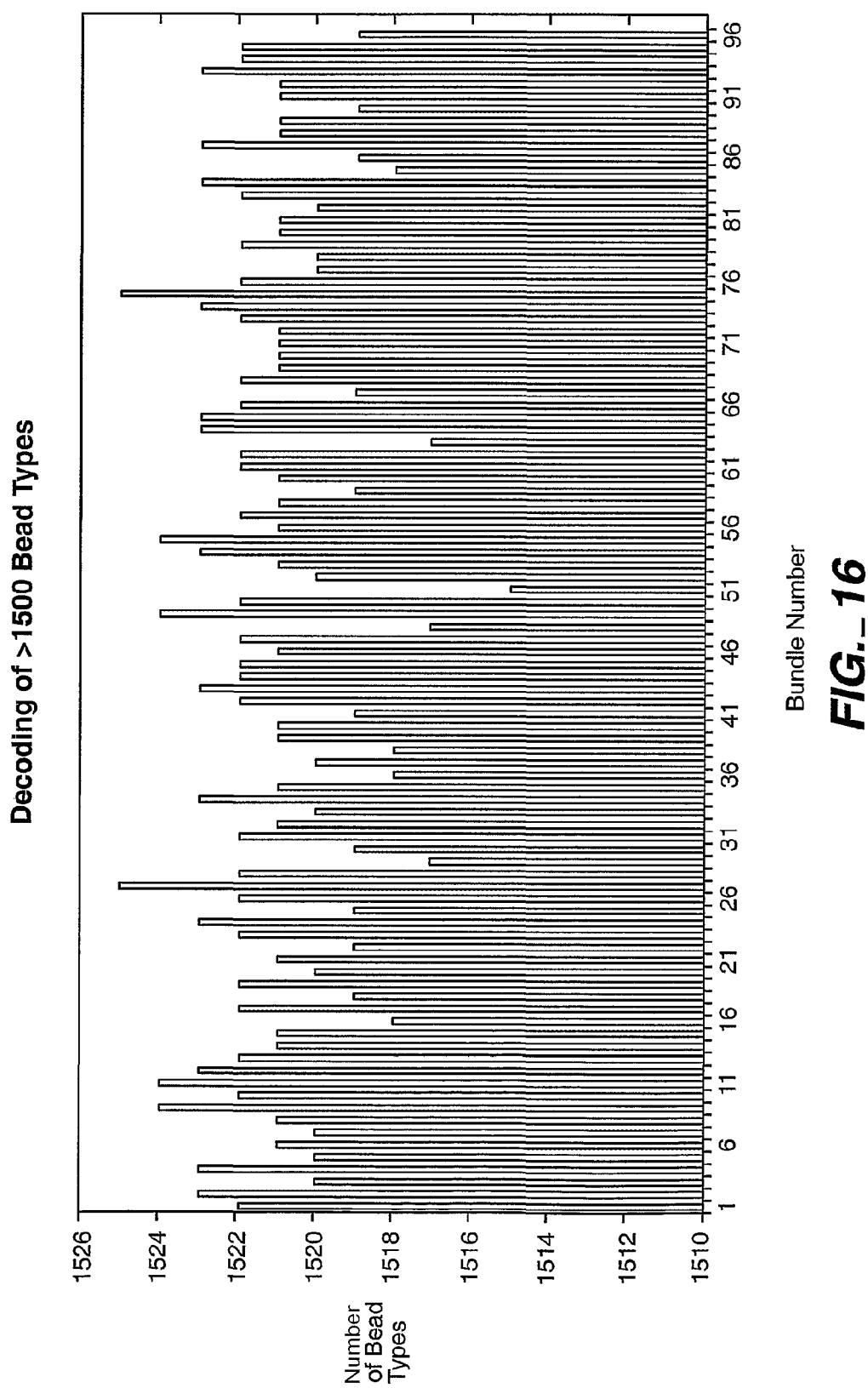
FIG._16

```
                              SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tgcacgagaa tggaggtatc t                                           21

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
ctgtcgcacg agaatggagg tatct                                       25

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
ctgtcggggc gcacgagaat ggaggtatct                                  30

<210> SEQ ID NO 4
<211> LENGTH: 34
<212> TYPE: DNA
<213> ORGANISM: Artificial Sequence
<220> FEATURE:
<223> OTHER INFORMATION: Synthetic

<400> SEQUENCE: 4
ctgtcggggc actcacacga gaatggaggt atct                             34

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
ctgtcggggc actcatttgt gcacgagaat ggaggtatct                       40

<210> SEQ ID NO 6
<211> LENGTH: 50
<212> TYPE: DNA
<213> ORGANISM: Artificial Sequence
<220> FEATURE:
<223> OTHER INFORMATION: Synthetic

<400> SEQUENCE: 6
ctgtcggggc actcatttgt ctgtcggggc gcacgagaat ggaggtatct            50
```

MULTIPLEX DECODING OF ARRAY SENSORS WITH MICROSPHERES

CROSS-REFERENCE TO RELATED APPLICATIONS

This application is a continuation of and claims priority to U.S. patent application Ser. No. 10/187,321, entitled MULTIPLEX DECODING OF ARRAY SENSORS WITH MICROSPHERES, filed Jun. 28, 2002, now U.S. Pat. No. 7,226,734, issued Jun. 5, 2007, which is a nonprovisional application of U.S. Provisional Application No. 60/302,213, filed Jun. 28, 2001; this application is also a continuation of U.S. patent application Ser. No. 11/285,722, filed Nov. 22, 2005 now U. S. Pat. No. 7,455,971, entitled MULTIPLEX DECODING OF ARRAY SENSORS WITH MICROSPHERES, which is a continuation-in-part of and claims priority to U.S. patent application Ser. No. 09/748,706, entitled DECODING OF ARRAY SENSORS WITH MICROSPHERES, filed Dec. 22, 2000, now U.S. Pat. No. 7,033,754, issued Apr. 25, 2006, which is a nonprovisional application of U.S. Provisional Application No. 60/235,531, filed Sep. 26, 2000 and U.S. Provisional Application No. 60/172,106, filed Dec. 23, 1999; both U.S. patent application Ser. Nos. 10/187,321 and 09/748,706 are continuation-in-part applications of and claim priority to U.S. patent application Ser. No. 09/344,526, entitled DECODING OF ARRAY SENSORS WITH MICROSPHERES, filed Jun. 24, 1999, now U.S. Pat. No. 7,060,431, issued Jun. 13, 2006, which is a continuation-in-part of and claims priority to U.S. patent application Ser. No. 09/189,543, entitled DECODING OF ARRAY SENSORS WITH MICROSPHERES, filed Nov. 10, 1998, now abandoned, which is a nonprovisional application of U.S. Provisional Application No. 60/090,473, filed Jun. 24, 1998.

REFERENCE TO SEQUENCE LISTING

The Sequence Listing provided herewith in electronic format was created on Apr. 24, 2007 as a 1.68 KB text file entitled ILLINC-PCP2CC_SeqListing.txt. This Sequence Listing is incorporated herein by reference in its entirety.

FIELD OF THE INVENTION

The invention relates to compositions and methods for decoding microsphere array sensors.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength, $_{ab}$; reach an excited energy state; and subsequently emit light at another light wavelength, $_{em}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analyses of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem.* 53:98 (1983); Lippitsch, et al., *Anal. Chem. Acta.* 205:1, (1988); Wolfbeis, et al., *Anal. Chem.* 60:2028 (1988); Jordan, et al., *Anal. Chem.* 59:437 (1987); Lubbers et al., *Sens. Actuators* 1983; Munkholm, et al., *Talanta* 35:109 (1988); Munkholm, et al., *Anal. Chem.* 58:1427 (1986); Seitz, W. R., *Anal. Chem.* 56:16A-34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun, et al., *Anal. Chem. Acta.* 160:47 (1984); Schwab, et al., *Anal. Chem.* 56:2199 (1984); Wolfbeis, O. S., "Fiber Optic Chemical Sensors", Ed. *CRC Press*, Boca Raton, Fla., 1991, 2nd Volume; and Pantano, P., Walt, D. R., *Anal. Chem.*, 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads go down randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

One drawback with the previous system is that it requires a set of unique optical signatures. While large sets of such signatures are available, for example by using different ratios of different dyes, it would be preferable to use decoding systems that do not rely on the use of sets of optical signatures. Accordingly, it is an object of the invention to provide methods to allow decoding of bead arrays without relying solely on unique optical signatures.

SUMMARY OF THE INVENTION

In accordance with the above objects, the present invention provides array compositions comprising a substrate with a surface comprising discrete sites. The composition further comprises a population of microspheres comprising at least a first and a second subpopulation; each subpopulation comprises a bioactive agent; and an identifier binding ligand that will bind a decoder binding ligand such that the identity of the bioactive agent can be elucidated. The microspheres are distributed on the surface.

In a further aspect, the present invention provides array compositions comprising a substrate with a surface comprising discrete sites, and a population of microspheres comprising at least a first and a second subpopulation. Each subpopulation comprises a bioactive agent and does not comprise an optical signature.

In an additional aspect, the present invention provides methods of making an array composition as outlined above. The methods comprise forming a surface comprising individual sites on a substrate and distributing microspheres on said surface such that said individual sites contain microspheres. The microspheres comprise at least a first and a second subpopulation each comprising a bioactive agent and do not comprise an optical signature.

In a further aspect, the invention provides methods of making a composition comprising forming a surface comprising individual sites on a substrate and distributing microspheres on the surface such that the individual sites contain microspheres. The microspheres comprise at least a first and a second subpopulation each comprising a bioactive agent and an identifier binding ligand that will bind a decoder binding ligand such that the identification of the bioactive agent can be elucidated.

In an additional aspect, the invention provides methods of decoding an array composition comprising providing an array composition as outlined above, and adding a plurality of decoding binding ligands to the array composition to identify the location of at least a plurality of the bioactive agents.

In a further aspect, the invention provides methods of determining the presence of a target analyte in a sample. The methods comprise contacting the sample with an array composition as outlined herein, and determining the presence or absence of the target analyte.

In a further aspect, the invention provides a method comprising providing an array composition comprising a population of microspheres comprising at least a first and a second subpopulation, wherein each subpopulation comprises a bioactive agent and at least a first and a second decoding attribute, and detecting each of said first and second decoding attributes to identify each of said bioactive agents.

In a further aspect the invention provides a method of increasing the information obtained in a decoding step. The method includes the use of degenerate probes as DBL-IBL combinations. In addition the invention provides the use of multiple decoding attributes on a bead.

In further aspect, the invention provides a method of increasing the confidence of decoding. The method includes using the decoding as a quality control measure. In addition, the invention provides quality control fibers. In addition, the invention provides for parity analysis of decoding data.

In a further aspect, the invention provides a method of decoding an array composition comprising providing an array composition comprising a population of microspheres comprising at least 50 subpopulations, wherein each subpopulation comprises a bioactive agent adding a plurality of decoding binding ligands to said population of microspheres to identify at least 50 of the bioactive agents.

In a further aspect, the invention provides a method of determining the presence of a target analyte in a sample comprising contacting said sample with a composition comprising a population of microspheres comprising at least 50 subpopulations, wherein each subpopulation comprises a bioactive agent adding a plurality of decoding binding ligands to said population of microspheres to identify at least 50 of the bioactive agents and determining the presence or absence of said target analyte.

FIGURES

FIG. 1 illustrates a two color decoding process wherein either FAM-labeled or Cy3-labeled oligo complements are use to "paint" (label) the different bead types on the array.

FIG. 2 depicts the decoding 128 different bead types with four colors and four decode stages. (inset shows a single decode stage using four different dyes to decode 16 bead types.)

FIG. 3 depicts grey scale decoding of 16 different bead types. (A) Combinatorial pooling scheme for complementary decoding oligos. A (B) Two independent normalizing images were acquired, and the resulting bead intensities compared. (C) The alpha values (ratio of bead intensity in indicated decode stage to intensity in normalization image) are plotted for three decodes stage described in (A).

FIG. 4 depicts the use of fluorescence resonance energy transfer as a code for a probe on a random array. A. Depicts FRET oligos with linkers of different lengths. B. Depicts a plot of the ration of emission of the fluors from the oligos in FIG. 4A.

FIG. 5 Use of fluorescence resonance energy transfer to discriminate between linkers of varying length. ET1 (SEQ ID NO: 1), ET2 (SEQ ID NO: 2), ET3 (SEQ ID NO: 3), ET4 (SEQ ID NO. 4), ET5 (SEQ ID NO: 5), ET7 (SEQ ID NO: 6).

FIG. 6 depicts clustering in hyperspectral alpha space ($\Delta_1 = I_1/6I_i$, $\Delta_2 = I_2/6I_i$, $\Delta_3 = I_3/6I_i$, etc.). A set of 128 different bead types present on a fiber bundle were decoded with hybridizing set of complementary oligonucleotides labeled with four dyes, Bodipy-493, Bodipy-R6G, Bodipy-TXR, and Bod-564 (only one dye per oligonucleotide). Shown is the second stage of a four stage decode in which 4013 beads were decoded. Ovals are drawn around zones of hue clusters.

FIG. 7 depicts an error checking scheme.

FIG. 8 depicts an example of primer extension labeling of decoder oligonucleotides.

FIG. 9 depicts two color decoding of 16 beads with 16 distinct IBLs.

FIG. 10 depicts primer extension labeling of degenerate IBL-DBL probes.

FIG. 11 depicts a scatter plot of signals obtained from three distinct labels recorded in two channels.

FIG. 12 depicts decoding by sequencing. A polymerase (e.g. Sequenase, Thermosequenase) and dye-labeled chain-terminating nucleotides are used to sequence the encoding region of a DNA strand present on the bead. The four nucleotides are each labeled with a discrete label. Because only 4 colors are detected at once, the colors are removed after each extension step. In subsequent extension steps, the primers are indexed or extended by one base so that the primer can query the next base in the encoding region.

FIG. 13 depicts construction of probes on bead containing encoding sequences, zipcodes, and a gene-specific sequence. Two different encoding cassettes are employed to facilitate the primer extension reaction using primers with universal or degenerate bases. Using four color sequencing and a single base code, 6 bases generates $4^6=4096$ codes, likewise four color hybridization using single hybridization colors also generates 4096 codes. The grand total number of codes is 4096*4096=>16 million. If only a single color/two state scheme is employed for hybridization, than $2^6=64$ codes are generated. The grand total is 4096*64=262,144 codes. The zipcode sequences can also be constructed so as to be overlapping to reduce the length of the overall sequence (i.e. cZip#1 vs. cZiP#2).

FIG. 14 depicts incorporation of a cleavable linker between encoding sequences and gene-specific sequence. A disulfide cleavable linker is shown for illustration purposes. If the linker is not present, the terminal portion of the gene-specific sequence can be included as part of the encoding sequence to reduce overall length of the probe.

FIG. 15 depicts decoding with exonuclease.

FIG. 16 depicts a graph showing decoding of about 1500 bead subpopulation on each of several different fiber bundles.

DETAILED DESCRIPTION OF THE INVENTION

The present invention is generally based on previous work comprising a bead-based analytic chemistry system in which beads, also termed microspheres, carrying different chemical functionalities are distributed on a substrate comprising a patterned surface of discrete sites that can bind the individual microspheres. Since the beads are generally put onto the substrate randomly, the previous work relied on the incorporation of unique optical signatures, generally fluorescent dyes, that could be used to identify the chemical functionality on any particular bead. This allows the synthesis of the candidate agents (i.e. compounds such as nucleic acids and antibodies) to be divorced from their placement on an array, i.e. the candidate agents may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or candidate agent at that particular site can be made. This means that the beads may be randomly distributed on the array, a fast and inexpensive process as compared to either the in situ synthesis or spotting techniques of the prior art.

However, the drawback to these methods is that for a large array, the system requires a large number of different optical signatures, which may be difficult or time-consuming to utilize. Accordingly, the present invention provides several improvements over these methods, generally directed to methods of coding and decoding the arrays. That is, as will be appreciated by those in the art, the placement of the bioactive agents is generally random, and thus a coding/decoding system is required to identify the bioactive agent at each location in the array. This may be done in a variety of ways, as is more fully outlined below, and generally includes: a) the use of decoding binding ligands (DBLs), generally directly labeled, that binds to either the bioactive agent or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target analyte. Similarly, this may occur either prior to or after addition of a target analyte.

Once the identity of the bioactive agent and its location in the array has been fixed, the array is exposed to samples containing the target analytes, although as outlined below, this can be done prior to or during the analysis as well. The target analytes will bind to the bioactive agents as is more fully outlined below, and result in a change in the optical signal of a particular bead.

In the present invention, "decoding" does not rely on the use of optical signatures, but rather on the use of decoding binding ligands that are added during a decoding step. The decoding binding ligands will bind either to a distinct identifier binding ligand partner that is placed on the beads, or to the bioactive agent itself, for example when the beads comprise single-stranded nucleic acids as the bioactive agents. The decoding binding ligands are either directly or indirectly labeled, and thus decoding occurs by detecting the presence of the label. By using pools of decoding binding ligands in a sequential fashion, it is possible to greatly minimize the number of required decoding steps.

In one embodiment, the invention provides methods for multiplex decoding of bead-arrays. That is, microspheres with bioactive agents are decoded to elucidate the identity of the bioactive agent on the bead. In a preferred embodiment at least 50 different bead types or subpopulations are simultaneously decoded, or decoded in a single decoding experiment. More preferably at least 100; more preferably at least 500; more preferably at least 1000; or preferably at least 1500 bead types are simultaneously decoded or decoded in a single decoding experiment by the methods of the invention. Preferably at least 5000 bead types are simultaneously decoded or decoded in a single decoding experiment.

Accordingly, the present invention provides array compositions comprising at least a first substrate with a surface comprising individual sites. By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000 (all numbers are per square cm), with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 m or less (with beads of 200 nm possible) can be used, and very small fibers are known, it is possible to have as many as 40,000 or more (in some instances, 1 million) different fibers and beads in a 1 mm$^2$ fiber optic bundle, with densities of greater than 15,000,000 individual beads and fibers (again, in some instances as many as 25-50 million) per 0.5 cm$^2$ obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT U.S.98/05025, and PCT U.S.98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, and WO 00/39587, both of which are hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the association of beads at any position. That is, the surface of the substrate is modified to allow association of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to associate, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic association of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow association of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either bioactive agent attachment or IBL attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending on the synthetic methods. By "candidate bioactive agent" or "bioactive agent" or "chemical functionality" or "binding ligand" herein is meant as used herein describes any molecule, e.g. protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 Daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365: 566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Biorganic & Medicinal Chem. Lett., 4:395 (1994); Jeffs, et al., J. Biomolecular NMR, 34:17 (1994); Tetrahedron Lett., 3 7:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

In a preferred embodiment, the bioactive agents are libraries of clonal nucleic acids, including DNA and RNA. In this embodiment, individual nucleic acids are prepared, generally using conventional methods (including, but not limited to, propagation in plasmid or phage vectors, amplification techniques including PCR, etc.). The nucleic acids are preferably arrayed in some format, such as a microtiter plate format, and beads added for attachment of the libraries.

Attachment of the clonal libraries (or any of the nucleic acids outlined herein) may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc.

In a preferred embodiment, affinity capture is used to attach the clonal nucleic acids to the beads. For example, cloned nucleic acids can be derivatized, for example with one member of a binding pair, and the beads derivatized with the other member of a binding pair. Suitable binding pairs are as described herein for IBL/DBL pairs. For example, the cloned nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach cloned nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

In general, special methods are required to decode clonal arrays, as is more fully outlined below.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarily need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis, et al., *Molecular Cloning: A Laboratory Manual,* 2d Edition, 1989, and *Short Protocols in Molecular Biology,* ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993). Generally, stringent conditions are selected to be about 5-10 C lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g. 10 to 50 nucleotides) and at least about 60 C for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, including beads, such as peptides, organic moieties, and nucleic acids.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc., is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, -haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctionallinkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems,* 7(4):275-308 (1991), expressly incorporated herein). Proteinaceous candidate agents may also be attached using other techniques known in the art, for example for the attachment of antibodies to polymers; see Slinkin et al., *Bioconj. Chem.* 2:342-348 (1991); Torchilin et al., supra; Trubetskoy et al., *Bioconj. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. Preferably, the manner of attachment does not significantly alter the functionality of the candidate agent; that is, the candidate agent should be attached in such a flexible manner as to allow its interaction with a target.

Specific techniques for immobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCI). This is stirred on a stir bed for approximately 2 hours at room temperature. The microspheres are then rinsed with ultrapure water plus 0.01% tween 20 (surfactant)-0.02%, and rinsed again with a pH 7.7 PBS plus 0.01% tween 20. Finally, the enzyme is added to the solution, preferably after being prefiltered using a 0.45 m amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids (including nucleic acid molecules that form triple helices), and carbohydrates and their binding partners are also suitable binding pairs. Nucleic acid—nucleic acid binding proteins pairs are also useful, including single-stranded or double-stranded nucleic acid binding proteins, and small molecule nucleic acid binding agents. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a protein, particularly an enzyme, that is conjugated to a bead. One advantage of using proteins/enzymes as IBLs is that many proteins and enzymes are commercially available in relatively pure preparations. Proteins contain many suitable functional groups for attachment to beads. Moreover, the identity of many small molecules including substrates that bind the proteins/enzymes are known. Such small molecules serve as the DBL. In addition, the small molecule can serve as the IBL and the enzyme as the DBL. As will be appreciated by those in the art, combinations of enzymes and small molecules can be used as well, or multiple enzymes and small molecules. Another potential advantage relates to the purification of the labeled proteins. If one conjugates a fluorophore to a recrystallizable protein, then the unlabeled protein can be removed from labeled protein by use of crystallization. By filtering off the crystalline solid, the labeled protein will be concentrated in the filtrate.

In an alternative embodiment, antigen-antibody pairs are used as DBL-IBL combinations. In one embodiment antibodies are conjugated to different labels, defined below, that are then used to decode antigen-labeled beads.

In a preferred embodiment, the IBL is a molecule whose color or luminescence properties change in the presence of a selectively-binding DBL.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the bioactive agent are the same moiety; thus, for example, as outlined herein, particularly when no optical signatures are used, the bioactive agent can serve as both the identifier and the agent. For example, in the case of nucleic acids, the bead-bound probe (which serves as the bioactive agent) can also bind decoder probes, to identify the sequence of the probe on the bead. Thus, in this embodiment, the DBLs bind to the bioactive agents. This is particularly useful as this embodiment can give information about the array or the assay in addition to decoding. For example, as is more fully described below, the use of the DBLs allows array calibration and assay development. This may be done even if the DBLs are not used as such; for example in non-random arrays, the use of these probe sets can allow array calibration and assay development even if decoding is not required.

In a preferred embodiment, the microspheres do not contain an optical signature. That is, as outlined in U.S. Ser. Nos. 08/818,199 and 09/151,877, previous work had each subpopulation of microspheres comprising a unique optical signature or optical tag that is used to identify the unique bioactive agent of that subpopulation of microspheres; that is, decoding utilizes optical properties of the beads such that a bead comprising the unique optical signature may be distinguished from beads at other locations with different optical signatures. Thus the previous work assigned each bioactive agent a unique optical signature such that any microspheres comprising that bioactive agent are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Thus, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use in combination with optical signatures one beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants. However, as is more fully discussed below, the size of the array may be further increased if another parameter is included such as concentration or intensity; thus for example, if two different concentrations of the IBL are used, then the array size increases as $3^n$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labeled DBL allows the user to distinguish between the two beads.

In addition, the use of different ratios of labeled to unlabeled IBLs allows for a differentiation of the intensity rather than the concentration of IBLs. For example, if a bead comprising a first agent has a ratio of 1:1 (labeled: unlabeled IBL), while a second bead comprising a second agent has a ration of 1:10 (labeled: unlabeled IBL), the user will distinguish the different intensities between the two beads. This procedure offers the advantage that a broad spectrum of intensities of labels can be created using only a single label.

Once the microspheres comprising the candidate agents and the unique IBLs are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target analytes, prior to the addition of the beads to the substrate; after addition and assay, the array may be decoded. This is particularly preferred when the sample comprising the beads is agitated or mixed; this can increase the amount of target analyte bound to the beads per unit time, and thus (in the case of nucleic acid assays) increase the hybridization kinetics. This may find particular use in cases where the concentration of target analyte in the sample is low; generally, for low concentrations, long binding times must be used.

In addition, adding the beads to the assay mixture can allow sorting or selection. For example, a large library of beads may be added to a sample, and only those beads that bind the sample may be added to the substrate. For example, if the target analyte is fluorescently labeled (either directly (for example by the incorporation of labels into nucleic acid amplification reactions) or indirectly (for example via the use of sandwich assays)), beads that exhibit fluorescence as a result of target analyte binding can be sorted via Fluorescence Activated Cell Sorting (FACS) and only these beads added to an array and subsequently decoded. Similarly, the sorting may be accomplished through affinity techniques; affinity columns comprising the target analytes can be made, and only those beads which bind are used on the array. Similarly, two bead systems can be used; for example, magnetic beads comprising the target analytes can be used to "pull out" those beads that will bind to the targets, followed by subsequent release of the magnetic beads (for example via temperature elevation) and addition to an array.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for association of the beads. This may be done in a variety of buffers, including aqueous and organic solvents, and mixtures. The solvent can evaporate, and excess beads removed.

In a preferred embodiment, when non-covalent methods are used to associate the beads to the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differential affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

In a preferred embodiment, the substrate is pressed into a mixture of dry beads (although slurries may be used as well), and then tapped to remove excess beads.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to associate the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface.

In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags, or mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of association of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Examples of such labels include: peroxidase; alkaline phosphatase; biotin; urease; E alactosidase; BSA/KLH; gold particles; quantum dots; redox indicators; pH indicators; E-lactamase; luciferase; TSA; SPA; chemiluminescence; sonoluminescence; fluorophores; phosphors; and, fluorescent metal ion sensors. Preferred labels include luminescent labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference. In addition, ion-sensitive dyes such as bis-BITC, Newport green, fluo 3, fura red find use in the invention.

In one embodiment, the label is a molecule whose color or luminescence properties change in the presence of the IBL, due to a change in the local environment. For example, the label may be: (1) a fluorescent pH indicator whose emission intensity changes with pH; (2) a fluorescent ion indicator, whose emission properties change with ion concentration; or (3) a fluorescent molecule such as an ethidium salt whose fluorescence intensity increases in hydrophobic environments.

In one embodiment ion sensitive dyes are used for decoding. That is, dyes that fluoresce in the presence of certain ions are used. In a preferred embodiment the ion sensitive dyes are attached to the beads. An advantage of attaching dyes directly to microspheres is that the cost associated with oligonucleotide synthesis is avoided.

Accordingly, when such dyes are attached to the beads they can be used to encode a specific nucleotide sequence, or the identity of the bioactive agent. Once the beads are distributed on the array, the array is contacted with buffers that include certain ions. In the presence of appropriate ion, certain dyes will fluoresce and fluorescence is detected. In a preferred embodiment, the array is contacted with different buffers sequentially. Each buffer contains a different ion. Preferably the array is washed between buffer solutions so that any signal produced as a result of the contact with the ion solution is diminished.

In this embodiment multiple different ion sensitive dyes can be used. That is, preferably, more than 2 with more than 3 or 4 dyes are attached to the microspheres. In some embodiments, more than 10 dyes are attached to the microsphere.

One advantage to using ion sensitive dyes is that fluorescence bleed-through is diminished. That is, because the response of the dyes is either positive or negative, i.e. they interact or they don't, bleed-through is avoided.

In a preferred embodiment, decoding of self-assembled random arrays is done on the basis of pH titration. In this embodiment, in addition to bioactive agents, the beads comprise optical signatures, wherein the optical signatures are generated by the use of pH-responsive dyes (sometimes referred to herein as "pH dyes") such as fluorophores. This embodiment is similar to that outlined in PCT U.S.98/05025 and U.S. Ser. No. 09/151,877, both of which are expressly incorporated by reference, except that the dyes used in the present invention exhibits changes in fluorescence intensity (or other properties) when the solution pH is adjusted from below the pKa to above the pKa (or vice versa). In a preferred embodiment, a set of pH dyes is used, each with a different pKa, preferably separated by at least 0.5 pH units. Preferred embodiments utilize a pH dye set of pKa's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the bioactive agent is generated. Thus, the decoding of an array is achieved by titrating the array from pH 1 to pH 13, and measuring the fluorescence signal from each bead as a function of solution pH.

In one embodiment, the decoder probes are labeled in situ; that is, they need not be labeled prior to the decoding reaction.

In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In one embodiment, a series of sequential extension and denaturing stages allows for positional decoding of the beads. That is, following one round of extension, the DBL is removed or stripped from the IBL and a second round of extension is performed. The contents of any given primer extension reaction is shown in FIG. 8.

In the primer extension method, up to four fluorescently-labeled dideoxynucleotide terminators each with a different colored label (e.g. using ABI's dRhodamine® terminators such as dR110, dR6G, dTAMRA, dROX or Big Dye® Terminators) could be used for 'painting.' The number of unique beads that can be decoded is given by $N=y^x$, where n=the number of unique codes, y=the number of colors and x=the number of stages or primer extension reactions. This formula yields 4096 unique codes using 6 primer extension stages and four colors (i.e. $4096=4^6$).

In a preferred embodiment the bioactive agent is synthesized with encoding sequences that allows decoding to be accomplished independent of the useable portion of the bioactive agent, i.e. nucleic acid sequence. By "useable" portion is meant the adapter sequence or target sequence. In a preferred embodiment the bioactive agent also is synthesized with a primer region to facilitate sequencing or primer extension analysis of the encoding sequence (see FIG. 12). As shown in FIG. 12, a primer complementary to a -portion of the ssDNA on the bead is extended by single base polymerase extension using dye-labeled chain terminating nucleotides. After incorporation of a labeled, i.e. fluorescent, chain terminator and reading of the array, i.e. detecting the label, the fluorescence is removed. Removal of the fluorescence is accomplished directly when reversible chain terminators are used (see Canard and Sarfati, Gene, 148(1): 1-6, 1994, which is expressly incorporated herein by reference). However, in a preferred embodiment the primer is dissociated from the bead and a subsequent primer is annealed. Preferably the subsequent primer is 1 nucleotide longer than the former primer so that an additional nucleotide in the encoding sequence can be interrogated. In a preferred embodiment the subsequent primer is lengthened by the addition of a degenerate base. This can be accomplished either by incorporating all 4 nucleotides into the additional position of the primer, or by the incorporation of a universal base into the primer. The new primer is then subject to extension as described above. The primer extension can be repeated as many times as are necessary to decode the microsphere.

Decoding by sequencing has the advantage that encoding a vast number of distinct codes by using only a small number of nucleotides. That is, the information content of the encoding region depends on the number of combinations of the bases used, i.e. 4 when A, C, G and T are used, that are present at each position and the length of the encoding region. When 4 nucleotides are used, there are up to fifteen possible combinations of nucleotides at each position (A, C, G, T, A/C, A/G, A/T, C/G, C/T, G/T, A/C/G, A/C/T, A/G/T, C/G/G and A/C/G/T). As such, the information content is $15^n$, where n is equal to the length of the encoding sequence. As such, for example, with just 3 base positions, 3375 different codes can be generated.

In addition an additional preferred embodiment includes the combination of decoding by sequencing with decoding by hybridization. In one application of decoding by sequencing, universal primers, each one base longer than the previous, are sequentially hybridized to the array. The base adjacent to the 3' end of the universal primer is determined by a single base extension reaction employing labeled-chain terminators, preferably using four different color labels one for each base. Since a hybridization event must be performed for each base read, once can improve the decoding power by using the hybridization event to also decode. However, rather than using universal primers, zipcode sequences would be used instead (see FIG. 13).

The placement of the encoding sequences can be either on the "bead-side" of the gene-specific sequence or on the terminal side. Placement of the encoding sequences on the terminal side offers that advantage of incorporating a cleavable linker between the encoding sequences and the gene-specific sequence (FIG. 14). After completion of decoding, the encoding sequences can be removed to prevent possible interference in the analytical assay.

In one embodiment following decoding, the label is extinguished. By "extinguished" is meant that the signal from the label is eliminated. This is accomplished by a variety of techniques including cleaving the label or destroying the signal of the label. That is, in one embodiment, the label is attached to the DBL via a cleavable linker. Following a decoding step, the linker is cleaved thereby releasing the label. In one embodiment cleavage of the label results in deprotection of the bioactive agent, for example when the bioactive agent contains a protecting group. Alternatively, cleavage of the label preserves the nature of the bioactive agent. That is, what is important is that cleavage of the label does not interfere with the bioactive agent.

In an alternative embodiment, the label is not cleaved, but rather is eliminated by destroying the signal of the label. That is, following decoding, the label is contacted with an agent that degrades or destroys the signal. For example, organic fluorescent dyes are subject to chemical degradation under appropriate conditions. Thus, following a decoding step where the fluorescent signal of the dyes are detected, the fluorophore is destroyed by an appropriate chemical solution that degrades the fluorescent molecule sufficient leaving no trace of fluorescence. In this way, beads are tagged with fluorescent labels, i.e. barcodes of sorts, their location or identity deciphered and recorded. The beads are then exposed to the "fluorescent destroying solution" and the fluorescence is eliminated, allowing an analytical assay to be conducted. Suitable fluorescent dyes include but are not limited to various bodipy, or Alexa dyes from Molecular Probes. The "fluorescent destroying solution" is a reducing or oxidizing solution, such as 0.01 SM sodium periodate.

In a preferred embodiment not only is the label cleaved, but the encoding nucleic acid is cleaved. This method finds particular use in removing residual signal following a decoding step. Accordingly, in a preferred embodiment a cleavable linker can be used to bridge the adapter and beads. After decoding, the adapter oligonucleotide(s) can be easily removed through cleavable linkers. There are many commercially available cleavable linkers. They are routinely used in the combinatorial solid-phase synthesis field. The linkers can be cleaved under acid, base or photo radiation conditions.

In addition, restriction enzymes can be used to cleave a linker. Alternatively, because of the sequence specificity of restriction enzymes, they also are used to cleave encoding nucleic acids. A change in signal following incubation with a sequence specific enzyme decodes the bead. An example is illustrative.

Consider the decoding of 6 bead types with three zip codes or adapters. In general, the strategy will have $B=(2^n)-2$. Where B is the number of types encoded and n is the number of zip codes. The bead types are z1, z2, z3, z1z2, z1z3, and z2z3. Here zizj indicates that both codes are on a bead. Every code is already dye labeled.

Generally, each code is designed with a site that can be specifically cut with some agent. This includes, but is not limited to, restriction enzymes. For ease of description, the process using restriction enzymes and zip codes that contain specific restriction sites is described. When restriction enzymes are used, the zip codes are double stranded. Each stage would consist of sequentially adding one restriction enzyme. An image is taken prior to stage 1, and the intensity of every bead is measured. Restriction enzyme 1 (Re1) is added. New intensity measurements are taken. The information of which beads decrease in intensity, and which remain the same. Detecting the pattern of beads for which the signal "decreased" and "stayed the same" uniquely determines the bead type. If we denote "decreased" by 1 and "stayed the same" by 0, then the decoding would give the following codes:

z1: 1,0,0
z2: 0,1,0
z3: 0,1
z1z2: 1,1,0
z1z3: 1,0,1
z2z3: 0,1,1.

The general approach uses n codes, which would give $(2^n)-2$ types. Subtracting 2 leaves off the all off state, and the all zip codes used state.

In another embodiment the array is decoded by using exonuclease enzyme. In this embodiment the microspheres are encoded with dye-labeled nucleotides. Preferably each nucleotide is labeled with a discrete label. In this particular embodiment it is desirable to protect the bioactive agent from cleavage. This can be accomplished by a variety of known methods including hybridizing the bioactive agent to a complementary sequence or blocking the terminus of the bioactive agent. Alternatively, if the exonuclease enzyme operates from 5' to 3', one can design zipcodes from 5' to 3' and SNP-gene specific oligos from 3' to 5'. This way zipcode sequences will be operated on by the exonuclease, but the SNP/gene-specific sequences will remain intact.

The microsphere is then contacted with an exonuclease that successively removes the labeled nucleotides of the encoding sequence. Monitoring of the signal of the microspheres should begin upon addition of the exonuclease and monitored in all channels that correspond to the signal emitted by the labels in use. For example, assume the microsphere has all the zipcodes available (with the above specifications), and is in a solution. At time T=0, the exonuclease enzyme is applied to the solution. At the same time, the acquisition system (CCD) starts taking images every few seconds (FIG. 15). The assumption is that the reaction of the exonuclease is slow enough, so one would have ample time to take several images, as the reaction is proceeding. If this is not the case, the reaction can be slowed down by increasing the stringency conditions.

The exonuclease removes the nucleotides, one at a time. Therefore, ideally, one would notice a step reduction in the signal of the appropriate channel, once the nucleotide is removed (and moved away from the focal zone). The complete set of waveforms (i.e., the four color channels, and from T0 to Tend) will provide a unique signature for every zipcode.

In practice, the removal of the nucleotides will not be completely synchronized on different oligos (as shown in FIG. 15). For instance, for two olligos on the same bead (same zipcode), the exonuclease may have removed one nucleotide from one, and two nucleotides from the other. However, since one monitors many olligos from each bead, the overall trend should be preserved, i.e., in general the nucleotides closer to the end should be removed first. This means that in general, although the transitions on the waveforms may not be sharp, the signatures could still be unique.

Accordingly, the identification of the location of the individual beads (or subpopulations of beads) is done using one or more decoding steps comprising a binding between the labeled DBL and either the IBL or the bioactive agent (i.e. a hybridization between the candidate probe (sometimes referred to herein as a "decoding sequence") and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used in an assay, during the assay, or after the assay.

In one embodiment, a single decoding step is done. In this embodiment, each DBL is labeled with a unique label, such that the number of unique labels is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique label, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. Each pool of decoders contains only one of the n tag versions of each decoder, and no two decoder probes have the same sequence of tags across all the pools. The number of pools required for this to be true is determined by the number of decoder probes and the n. Hybridization of each pool to the array generates a signal at every address comprising an IBL. The sequential hybridization of each pool in turn will generate a unique, sequence-specific code for each candidate probe. This identifies the candidate probe at each address in the array. For example, if four tag's are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc.

As will be appreciated by those in the art, the decoder probes can be made in any order and added in any order.

In addition, since the size of the array will be set by the number of unique decoding binding ligands, there are a number of techniques that allow new combinations and the "reuse" of DBLs to allow for a greater number of test sites. This may be done in a wide variety of ways, as outlined below.

In a preferred embodiment, a spatial or positional coding system is done. In this embodiment, there are sub-bundles or subarrays (i.e. portions of the total array) that are utilized. By analogy with the telephone system, each subarray is an "area code", that can have the same labels (i.e. telephone numbers) of other subarrays, that are separated by virtue of the location of the subarray. Thus, for example, the same unique labels can be reused from bundle to bundle. Thus, the use of 50 unique labels in combination with 100 different subarrays can form an array of 5000 different bioactive agents. In this embodiment, it becomes important to be able to identify one bundle from another; in general, this is done either manually or through the use of marker beads; these can be beads containing unique tags for each subarray, or the use of the same marker bead in differing amounts, or the use of two or more marker beads in different ratios.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sub library comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc., sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes or "families" of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In a preferred embodiment, the set of codes can be increased using a kind of degeneracy on the IBLs on the beads. For most of the systems described herein, particularly when the IBL is a nucleic acid (including the case where the nucleic acid IBL is also the candidate agent), any single bead contains a single IBL sequence (decoding sequence). However, in this embodiment, it is possible to have a single bead comprise two or more decoding sequences, that differ at a particular nucleotide position. For a degeneracy of two at position X, there are 10 different possible combinations: the decoding sequence has an A at position X, a T, a C, a G, or a mixture of decoding sequences with either A/T, A/G, A/C, C/G, C/T or G/T. By using decoder probes that have different labels for each different nucleotide at the position, the number of codes can be increased, since beads containing the two different sequences will exhibit a mixture of signals. In addition, as will be appreciated by those in the art, rather than a "degeneracy" of two, degeneracies of three or four can be done as well. Thus, a bead containing three different decoding sequences will exhibit a signal comprising three different colors, etc.

Decoding the degenerate probes is done by a series of hybridizations to labeled oligonucleotides. Each hybridization decodes one position in the probe so the total number of hybridizations needed to decode a library is equal to the length of the variable region. Each hybridization is done with four oligonucleotides, each designed to hybridize specifically to a sequence containing a specific base at the interrogated position and each tagged with a distinctly colored fluorescent dye.

In a preferred embodiment, a degenerate probe sequence is attached to one or more constant probe regions. By "constant" probe region is meant a portion of a probe that is invariant among a population of decoder probes. In a particularly preferred embodiment, the degenerate or variable region is flanked on either side by constant regions. As such, each oligonucleotide has the following structure:

| C1 "constant" region | V "variable" region | C2 region |
|:---:|:---:|:---:|
| C1 | NNN... | C2 |

Although the C1 and C2 regions may be any length, preferably each is from 5 to 50 nucleotides in length. More preferably each is from 7 to 30 nucleotides in length and most preferably, each is about 10 bp in length. In one embodiment, the constant regions do not vary in sequence among the probes designed to decode a particular set of beads. As such, by using constant and variable regions (i.e. "CV" or "CVC" when two constant regions are used) in a set of probes, an array specific set or library of probes is generated.

The variable region contains a sequence that is unique to each address. Each "N" or variable position within the variable region can contain one of ten possibilities as described above. As such, the number of unique addresses in a library is determined by the length of the variable region: if L is length of the variable region, the number of unique addresses, A, is $A=10^L$.

Accordingly, decoding the first base of the variable region of a decoding sequence is illustrated below:

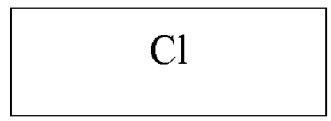 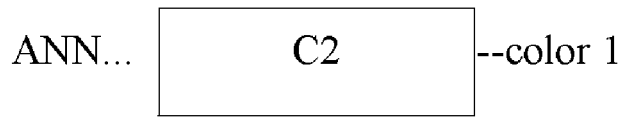 —color 1
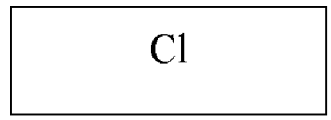 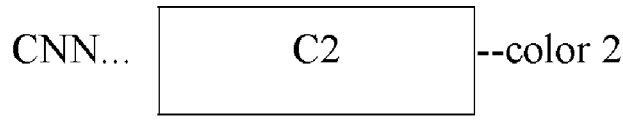 —color 2
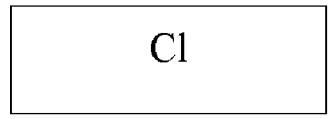 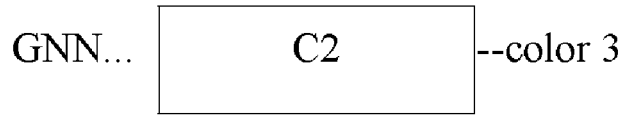 —color 3
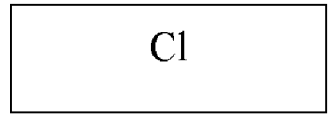 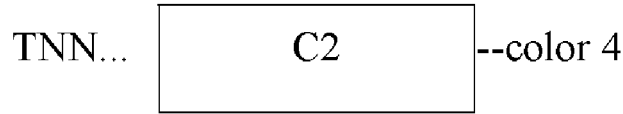 —color 4

Any address with an A at the first position would hybridize with the fourth oligonucleotide and give the corresponding color. An address with an A/C at the first position would hybridize with both the third and fourth decoders and give the corresponding combination of colors. By serial hybridizations, each using four decoders and each interrogating a different position of the Y region, the entire sequence of each address can be determined. The "N" positions in the decoders are synthesized with degeneracies of the four standard bases.

In one embodiment, CVC probes are incorporated into the probes of an oligonucleotide array during synthesis as is described for the addition of adapters; see U.S. Ser. Nos. 09/553,993, filed Apr. 20, 2000, 09/556,463, filed Apr. 21, 2000, 60/160,917, filed Oct. 22,1999, and 60/135,123, filed May 20, 1999 and WO 00/63437, all of which are expressly incorporated herein by reference. In a similar fashion, the CVC probes could be synthesized in the 5-prime ends of PCR primers used to generate a PCR-product-based array. By incorporating different probes into the two primers of each PCR reaction, a combinatorial expansion of addresses is possible:

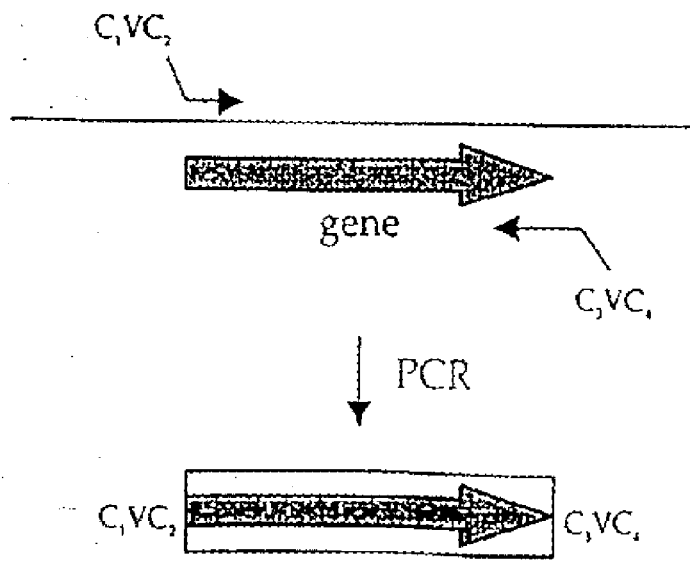

The constant regions in the $C_1VC_2$ addresses would be different in sequence from the $C_3VC_4$ addresses. Each would therefore be decoded with its own set of CVC complement decoders. If $C_1VC_2$ has a 3-base V region (1000 addresses) and $C_3VC_4$ has a 3-base V region (1,000 addresses), then the combination results in 1,000×1,000, or one million addresses.

In a preferred embodiment, there are additional ways to increase the number of unique or distinct tags. That is, the use of distinct attributes on each bead can be used to increase the number of codes. In addition, sequential decoding allows a reuse of codes in new ways. These attributes are independent of each other, thus allowing the number of codes to grow exponentially as a function of the number of decoding steps and the number of attributes (e.g. distinct codes). However, by increasing the amount of decoding information obtained in a single decoding step, the number of decoding steps is markedly reduced. By increasing the number of attributes per decoding step, fewer decoding steps are required for a given number of codes. Thus, in a preferred embodiment, a variety of methods are used to generate a number of codes for use in the process of decoding the arrays, while minimizing the necessary decoding steps. For example, a variety of different coding strategies can be combined: thus, different "colors", combinations of colors ("hues"), different intensities of colors or hues or both, different colors and different bead sizes, etc. can all be combined. Alternatively, the number of distinct codes is markedly increased.

In a preferred embodiment DBLs rely on attaching or embedding a quantitative or discrete set of physical attributes to the bead, i.e. labeling the bead. Preferred physical attributes of a bead include but are not limited to: surface "smoothness" or "roughness", color (fluorescent and otherwise), color intensity, size, detectable chemical moieties, chemical reactivity, magnetization, pH sensitivity, energy transfer efficiency between dyes present, hydrophobicity, hydrophilicity, absorptivity, charge, pH sensitivity, etc. In general, physical attributes that can be measured optically are preferred, including color, size, surface smoothness etc.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include those listed for labeling DBLs, above.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres In the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

A bead decoding scheme includes assigning/imbuing a single quantifiable attribute to each bead type wherein each bead type differs in the quantifiable value of that attribute. For instance, one can attach a given number of fluorophores to a bead and quantitate the number of attached fluorophores in the decoding process; however, in practice, attaching a "given amount" of an attribute to a bead and accurately measuring the attribute may be problematic. Typically, the coefficient of variation (CV) seen in associating an attribute and the resultant measurement of this attribute is quite large (>20%). By coefficient of variation is meant the variability in labeling a bead in successive labelings. This CV can be determined by labeling beads with a defined given number of label (fluorophore, for example) in multiple tests and measuring the resulting signal emitted by the bead. This large CV limits the number of useable and resolvable "levels" for any given attribute.

A more robust decoding scheme employs ratiometric rather than absolute measurements for segmenting a quantitative attribute into codes. By ratiometric decoding is meant labeling a bead with a ratio of labels or attributes (i.e. 1:10, 1:1, and 10:1). In theory any number of ratios can be used so long as the difference in signals between the ratios is detectable. This process produced smaller CVs and allowing more attribute segmentation within a given dynamic range. Thus, in a preferred embodiment, the use of ratiometric decoding reduces the coefficient of variability.

In addition, as will be appreciated by those in the art, ratiometric decoding can be accomplished in a different way. In this embodiment, rather than add a given number of beads with a first dye (or dye combination) intensity in the first decoding reaction and a second number with a second dye intensity in the sequential second decoding reaction, this ratiometric analysis may be done by using a ratio of labeled:unlabeled beads. That is, given a set saturating concentration of decoding beads, for example 100,000 beads/reaction, the first intensity decoding step may be done by adding 100,000 labeled beads and the second step can be done by adding 10,000 labeled beads and 90,000 unlabeled beads. Equilibrium dictates that the second step will give one tenth the signal intensity.

Because of the spread in values of a quantitatively measured attribute value, the number of distinct codes is practically limited to less than a dozen or so codes. However, by serially "painting" (i.e. temporarily attaching an attribute level to a bead) and "stripping" (removing the attribute level) a bead with different attribute values, the number of possible codes grows exponentially with the number of serial stages in the decoding process.

An example is illustrative. For instance, 9 different bead types and three distinguishable attribute distributions (Table 1). "Painting" (labeling) the beads with different attribute values in a combinatorially distinct pattern in the two different stages, generates a unique code for each bead type, i.e. nine distinct codes are generated. Thus, in a preferred embodiment beads are labeled with different attributes in a combinatorially distinct pattern in a plurality of stages. This generates unique codes for each bead type. Examples of different attributes are described above. Labeling of beads with different attributes is performed by methods known in the art.

TABLE 1

Serial decode generates unique codes using a small number of attribute levels.

| Bead Type | stage 1 Attribute Value | stage 2 Attribute Value | Code |
|---|---|---|---|
| 1 | L | L | (L, L) |
| 2 | L | M | (L, M) |
| 3 | L | H | (L, H) |
| 4 | M | L | (M, L) |
| 5 | M | M | (M, M) |
| 6 | M | H | (M, H) |
| 7 | H | L | (H, L) |
| 8 | H | M | (H, M) |
| 9 | H | H | (H, H) |

Number of unique codes = Number of attributes – Number of stages

As outlined herein, fluorescent colors are a particularly convenient and preferable attribute to use in a decoding scheme. Fluorescent colors can be attached to any agent that recognizes an IBL to form a labeled DBL. A fluorescently labeled oligonucleotide is a particularly useful DBL since it can specifically and reversibly "paint" (label) any desired subset of beads with a particular color simply by the process of hybridization and dehybridization (i.e. to the DBL with a complementary sequence). Moreover, fluorescence is easily damaged and quantitated using standard optical hardware and software. In order to "paint" a given bead type with a particular color, the bead type must be labeled with a unique hybridizable DNA sequence (IBL) and the decoding solution must contain the color-labeled complement of that sequence.

One consideration in implementing a decoding scheme is to minimize the number of images collected. In a color-based scheme, the number of images collected is the product of the number of colors and the number of stages. The number of images can be reduced by "painting" a bead with multiple colors for each given stage. By assigning multiple colors to a bead, the number of effective codes is increased. As an example, in a 24 bit three color scheme (e.g. red, green, blue) coloring process used by computers, a total of 256*256*256=16.7 million different "hues" can be generated from just three colors (red, green, blue).

Thus, in a preferred embodiment DBLs are labeled with a combination of colored fluorophores. As such, this method finds use in increasing the number of available codes for labeling DBLs using only a handful of different dyes (colors). Increasing the number of codes available at each decoding step will greatly decrease the number of decoding steps required in a given decoding process.

In one embodiment a population of oligonucleotides encoding a single DBL is labeled with a defined ratio of colors such that each bead to which the DBL binds is identified based on a characteristic "hue" formulated from the combination of the colored fluorophores. In a preferred embodiment two distinct colors are used. In a preferred embodiment, three or more distinct dyes (colors) are available for use. In this instance the number of differentiable codes generated by labeling a population of oligonucleotides encoding a single DBL with any given color is three. However by allowing combinations of colors and color levels in the labeling, many more codes are generated.

For decoding by hybridization, a preferred number of distinguishable color shades is from 2 to 2000; a more preferred number of distinguishable color shades is from 2 to 200 and a most preferred number of distinguishable color shades is from 2 to 20. Utilizing three different color shades (intensities) and three colors, the number of different hues will be $3^4=81$. Combining a hue with sequential decoding allows a virtually limitless number of codes to be generated.

As previously described, the DBL can be any agent that binds to the IBL. In a preferred embodiment, a single DBL is labeled with a pre-determined ratio of colors. This ratio is varied for each DBL thus allowing for a unique "hue" for each DBL labeled as such. Following treatment of the beads with the DBL, the bead is analyzed to determine the "hue" associated with each bead, thereby identifying the bead with its associated bioactive agent.

For instance, with four primary colors and two intensity levels (color is present or absent), fifteen different hues/stage are possible. If four dyes and three different intensity levels are used (absent, half-present, fully present), then 73 different hues/stage are possible. In this case, acquisition of only 4 color images is sufficient to obtain information on 73 different coding hues.

In a preferred embodiment the DBL relies on a Fluorescence Resonance Energy Transfer (FRET) identifier. Fluorescence resonance energy transfer (FRET) is well known in the art and has been employed for various biotechnological applications. FRET requires that the energy of the donor excited state overlap with the ground state of the acceptor, implying that the donor emission spectrum overlaps with the acceptor absorbance spectrum. In a FRET experiment, the donor is excited with light; some of the energy of the excited state is released as light emission while some of the energy is transferred to the acceptor, which becomes excited emitting light at a characteristic wavelength. The distance over which energy transfer may occur can be varied by the choice of energy donor and acceptor, wherein the use of various different donor and acceptor molecules is contemplated. The formula for the efficiency of energy transfer is:

$$T=R_0^6/(R_0^6+R^6)$$

Where R is the distance between the donor and acceptor, and $R_0$ is a constant related to the characteristic overlap of the absorption and emission spectra of the donor-acceptor pair.

A FRET identifier comprises a linker region that is labeled at each terminus with a fluorophore. The first fluorophore serves as a donor fluorophore, whose signal is detectable; the other acts as an acceptor fluorophore. The emission of the acceptor fluorophore also is a detectable signal, the intensity of which varies proportionally with the distance between the two fluorophores. That is, by varying the distance between the two fluorophores different codes can be generated.

Identification of the decoding oligonucleotide, therefore, is accomplished by identifying the "efficiency" or ratio of intensities of the acceptor fluorophore and the donor fluorophore. This ratio should be invariant with regard to the number of decoding oligonucleotides bound to a particle (bead); rather, without being bound by any theory, the distance between the fluorophores determines the ratio. Thus, by varying the distance between the fluorophores (i.e. increasing or decreasing the length of the linker), unique "codes" can be assigned to the DBLs. Each code is characterized by the ratio of emission intensities between the two fluorophores.

An even greater advantage is realized when different bead attributes can be collected in a single image rather than from multiple images. For instance, if the colors of red, green and blue are used as attributes, three separate images need to be collected. However, if different shades or intensities of each color are used in the coding process, a much larger number of attributes can be realized in a single image. The difficulty with using mixtures of colors, is that the color ratios can vary somewhat between bead types since individual components are mixed together to determine the color ratio. If on the other hand, the color ratio is built into the decoding label, as with the above described FRET decoding oligonucleotides, the decoding process should be more reliable and more efficient.

In preferred embodiments of the present invention, the first component may be a lanthanide such as a chelate of europium (III) (Eu(III)) or terbium(III) (Tb(III)) which serves as a fluorescent donor and the second component may be an activated ester of cyanine 5 (Cy5) or tetramethylrhodamine (TMR) which serve as energy acceptors of Eu(III) and Tb(III). Other first and second component pairs that will find use for FRET include, for example, fluorescein and rhodamine; FITC and rhodamine; and fluorescein and trinitrophenyl, and other components as are well known In the art.

The linker is comprised of any spacer element including alkyl linkers, polymer linkers, etc. For ease of synthesis, preferably the linker comprises nucleic acids (including nucleic acid analogs).

The FRET decoding oligonucleotide comprises a spacer or linker region that is labeled with fluorophores (dyes). In general, this may be used in two general ways. In a preferred embodiment, as generally depicted in FIG. 4, the linker is attached to the terminus of a decoding nucleotide that hybridizes with (is complementary to) the IBL. In this embodiment, the linker length can be varied to adjust signal intensity. Thus, in a preferred embodiment a FRET oligonucleotide is adjoined to an oligonucleotide DBL. In one embodiment the FRET oligonucleotide is synthesized independent of the DBL oligo. Subsequently the FRET oligonucleotide is ligated to the DBL oligo according to methods well known in the art. Alternatively, the DBL oligo and FRET oligo are synthesized as a single oligonucleotide comprising the FRET fluorophores at the desired positions.

Alternatively, in a second embodiment the linker is itself the oligonucleotide that hybridizes with (is complementary to) the IBL. That is, fluorophores are attached to the decoding oligonucleotide at different basepair lengths; some may be 10 nucleotides apart, some 20, etc. In a preferred embodiment the oligonucleotide DBL is itself labeled with fluors; as such the oligonucleotide serves as both DBL and FRET oligonucleotide.

The linker region of a FRET oligonucleotide comprises any set of nucleotides; in a preferred embodiment, for example when the linker does not hybridize to anything, the linker comprises a single repeated nucleotide. A single repeated nucleotide is less likely to hybridize with the IBL or bioactive agent on the bead because of the reduced likelihood of the presence of a complementary nucleotide sequence in either the IBL or bioagent on the bead. In a preferred embodiment, the linker comprises a polynucleotide linker such as poly T, poly A, poly G or poly C, or combinations.

The linker can be of any length so long as the emission of the first fluorophore is absorbed by the second fluorophore. In a preferred embodiment the linker is formed of from 1 to at least 100 nucleotides. More preferably the linker is formed from 1 to 70 nucleotides. Most preferably the linker is formed from 1 to 40 nucleotides, with from 5 to 20 being especially preferred.

In a preferred embodiment, for a given DBL sequence, several codes can be generated by varying the distance of separation of the two fluorophores and hence generating several energy transfer "efficiency" ratios.

In another preferred embodiment, for a given DBL sequence, a single code can be generated by varying the distance of separation of the two flourophores and hence generating a single energy transfer ratio for a single DBL. However, numerous DBLs can be labeled with distinct FRET oligos thus allowing for the simultaneous determination or identification of multiple DBLs in a single imaging session as a result of the plurality of energy transfer ratios.

For example, given a 40-mer decoding oligo, the donor and acceptor fluorophores can be located as close as one or as far apart as 40 bases. In principle this should allow 39 codes to be generated for a single decoding sequence. Empirically, the number of codes generated depends on dispersion in the distributions for the ratiometric measurements.

Also, given a 40-mer decoding oligo, 39 unique codes can be generated which will identify 39 different oligos.

The present invention provides array compositions comprising a substrate with a surface comprising discrete sites. A population of microspheres is distributed on the sites, and the population comprises at least a first and a second sub population. Each subpopulation comprises a bioactive agent, and, in addition, at least one optical dye with a given pKa. The pKas of the different optical dyes are different.

In a preferred embodiment, when for example the array comprises cloned nucleic acids, there are several methods that can be used to decode the arrays. In a preferred embodiment, when some sequence information about the cloned nucleic acids is known, specific decoding probes can be made as is generally outlined herein.

In a preferred embodiment, "random" decoding probes can be made. By sequential hybridizations or the use of multiple labels, as is outlined above, a unique hybridization pattern can be generated for each sensor element. This allows all the beads representing a given clone to be identified as belonging to the same group. In general, this is done by using random or partially degenerate decoding probes, that bind in a sequence-dependent but not highly sequence-specific manner. The process can be repeated a number of times, each time using a different labeling entity, to generate a different pattern of signals based on quasi-specific interactions. In this way, a unique optical signature is eventually built up for each sensor element. By applying pattern recognition or clustering algorithms to the optical signatures, the beads can be grouped into sets that share the same signature (i.e. carry the same probes).

In order to identify the actual sequence of the clone itself, additional procedures are required; for example, direct sequencing can be done. By using an ordered array containing the clones, such as a spotted cDNA array, a "key" can be generated that links a hybridization pattern to a specific clone whose position in the set is known. In this way the clone can be recovered and further characterized.

Alternatively, clonal arrays can be decoded using binary decoding with vector tags. For example, partially randomized oligos are cloned into a nucleic acid vector (e.g. plasmid, phage, etc.). Each oligonucleotide sequence consists of a subset of a limited set of sequences. For example, if the limited set comprises 10 sequences, each oligonucleotide may have some subset (or all of the 10) sequences. Thus each of the 10 sequences can be present or absent in the oligonucleotide. Therefore, there are $2^{10}$ or 1,024 possible combinations. The sequences may overlap, and minor variants can also be represented (e.g. A, C, T and G substitutions) to increase the number of possible combinations. A nucleic acid library is cloned into a vector containing the random code sequences. Alternatively, other methods such as PCR can be used to add the tags. In this way it is possible to use a small number of oligo decoding probes to decode an array of clones.

There are a variety of methods used to evaluate decoding. In a preferred embodiment, discriminant analysis and cluster algorithms and computer apparatus are used to analyze the decoding data from the arrays of the invention. The potentially large number of codes utilized in the invention, coupled with the use of different intensities and "hues" of fluorophores in multi-step decoding processes, requires good classification of the data. The data, particularly intensity data, is acquired in a multi-step process during which beads are "painted" (for example by hybridizing dye-labeled complementary decoding oligonucleotides to the IBL probes on the beads, or the formation of binding ligand pairs for non-nucleic acid IBL-DBL pairs) with different colors or mixtures of colors ("hues") at each stage. The challenge is to accurately classify a bead as to which color with which it was painted at each step. The more closely related the "paints" (colors) are to one another (as determined by the optical imaging system), the more difficult the classification.

The proximity of the dyes as seen by the imaging system is determined by the spectral properties of the decoding dyes and the spectral channel separation of the imaging system. Better color separation is achieved by employing fluorescent dyes with narrow emission spectra, and by employing an optical system with narrow band pass excitation and emission filters which are designed to excite the dye "on peak" and measure its emission "on peak". The process of optically imaging the dyes on the beads is similar to the human vision process in which our brain sees color by measuring the ratio of excitation in the three different cone types within our eye. However, with an optical imaging system, the number of practical color channels is much greater than the three present in the human eye. CCD based imaging systems can "see" color from 350 nm up to 850 nm whereas the cones in the eye are tuned to the visible spectrum from 500- 600 nm.

The problem of decoding bead arrays is essentially a discriminant analysis classification problem. Thus, in a preferred embodiment, an analysis of variance in hyperspectral alpha space is performed on a known set of bead colors or hues. The center of the bead clusters in alpha space are termed the centroids of the clusters, and the scatter of the points within a cluster determines the spread of the cluster. A robust classification scheme requires that the distance between the centroids of the different bead classes (hues) is much greater than the spread of any cluster class. Moreover, the location of the centroids should remain invariant from substrate to substrate and from experiment to experiment.

Thus, in a preferred embodiment, a hue "zone" is defined as a region in alpha space surrounding the hue centroid and extending out to the spread radius of the cluster. Given a reference set of hue centroids and spread radii, as determined empirically, the classification of a new set of data can be accomplished by asking whether a given bead point falls closest to or within the "zone" of a hue cluster. This is accomplished by calculating the Mahalanobis distance (in this case, it is simply a Euclidean distance metric) of the bead point from the centroids of the different hue classes. For the data shown in FIG. 6, the location of the centroids and their distances from one another are indicated in Table 2.

TABLE 2

| dye/ channel | Centroid position | | | | Distance between centroids | | | |
|---|---|---|---|---|---|---|---|---|
| | Blue | Green | Yellow | Red | Bod-493 | Bod-R6G | Bod-564 | Bod-TXR |
| Bod-493 | 0.63 | 0.22 | 0.11 | 0.03 | 0.00 | | | |
| Bod-R6G | 0.03 | 0.51 | 0.37 | 0.09 | 0.72 | 0.00 | | |
| Bod-564 | 0.06 | 0.04 | 0.57 | 0.32 | 0.81 | 0.55 | 0.00 | |
| Bod-TXR | 0.09 | 0.05 | 0.04 | 0.82 | 0.99 | 0.93 | 0.73 | 0.00 |

For classifying the different beads into a particular hue class, a Euclidean distance cutoff of 0.3 was chosen. The closest two centroids, the Bod-R6G and Bod-564 (dist=0.55), have a slight overlap in their decoding zones when using a Euclidean or Mahalanobis distance of 0.3. An improvement in classification can be achieved by decreasing this distance, and by weighting the different coordinate axes appropriately.

Accordingly, the present invention provides computer methods for analyzing and classifying the color of a bead. The classification of the color of the bead is done by viewing the bead in hyperspectral "alpha" space ($\Delta_1=I_1/6I_i$, $\Delta_2=I_2/6I_i$, $\Delta_3=I_3/6I_i$, etc.) in which each coordinate axis represents the fraction of the bead intensity within a given imaging channel. For instance, if four imaging channels are used to image the beads, the color or hue of a bead can be represented by a point in 3-D alpha space (the fourth dimension is not necessary since $Sa_i=1$). Given a set of different primary dyes by which to "paint" the beads, the number of hues that can be generated from these dyes is unlimited since these dyes can be combined in varying ratios and in varying combinatorial patterns. The number of practical hues is experimentally determined by the separation of the different hue clusters in hyperspectral alpha space.

FIG. 6 shows a hyperspectral alpha plot of beads "painted" with four different hues imaged in four separate imaging channels. Note that the beads form four distinct clusters. The fact that these four clusters are well separated allows a robust decode classification scheme to be implemented.

In a preferred embodiment, a quality control analysis of the decoding process is done. This is achieved by performing a cluster analysis of alpha space for each decoding stage. The number of clusters determined will be fixed by the expected number of hues. The positions of the cluster centroids will be monitored and any deviations from the expected position will be noted.

Thus the invention provides an apparatus for decoding the arrays of the invention. In addition to the compositions outlined herein, the apparatus includes a central processing unit which communicates with a memory and a set of input/output devices (e.g., keyboard, mouse, monitor, printer, etc.) through a bus. The general interaction between a central processing unit, a memory, input/output devices, and a bus is known in the art. One aspect of the present invention is directed toward the hyperspectral "alpha" space classification system stored in the memory.

The classification system program includes a data acquisition module that receives data from the optical reader or confocal microscope (or other imaging system). In general, the classification program also includes an analysis module, that can analyze the variance in hyperspectral alpha space, calculate the centroids of the clusters, calculate the scatter of the cluster (the spread) and define the hue zone and distance cutoff In general, the analysis module will further determine whether a data point falls within the hue zone by calculating the Mahalanobis distance.

Finally, the analysis module will analyze the different sequential decoding information to finally assign a bioactive agent to a bead location.

In this way, sequential decoding steps are run, with each step utilizing the discriminant analysis calculations to assign each bead in the array to a hue cluster at each step. The buildup of the sequential decoding information allows the correlation of the location of a bead and the chemistry contained on it.

In one embodiment, the invention includes modifying the number of detection channels available for analysis relative to the number of labels to be detected. That is, in one embodiment, the number of detection channels is decreased relative to the number of labels used. In an alternative embodiment the number of detection channels is increased relative to the number of labels used.

When fewer detection channels are used, fewer images are required during decoding. As such the invention provides a method of reducing the number of images obtained during decoding. Fluorescent dyes have broad band absorption and emission spectra. Accordingly, the emission of certain dyes is detected in multiple channels, generally by choosing channels to maximize the signal. However by choosing the dyes and the channels carefully, fewer channels that dyes may be used. As such, decoding with fewer channels than dyes, allows for detection of signals that are maximally detected in a particular channel, and overlapping in several channels. Thus, for example, beads with dye-1 are read in channel-1, beads with dye-2 are read in channel-2 and beads with dye-3 show signals in both channel-1 and channel-2. Example 7 is illustrative and the results of the experiment are found in FIG. 11. It is noted, however, that three dyes are clearly detected and distinguished following detection in only two channels. Accordingly, using fewer detection channels than the number of dyes to be analyzed, allows for a reduction in the number of images and steps required for decoding.

In an alternative embodiment, the invention provides for using additional channels to increase the number of detectable codes. That is, additional readout channels are used to increase the coding/decoding capacity of arrays by analyzing attributes of the bead in addition to an optical signal such as fluorescence. For example, bead size, shape, density and surface characteristics can alter the light-scattering properties of the beads and can be detected optically. Additional channels that provide information independent of fluorescence are forward-scatter and side-scatter. Low-angle forward light scatter provides some information on the relative size of beads, whereas side light scatter provides some information on the relative granularity or texture of individual beads. By analogy these channels are often used in combination to distinguish the different major categories of white cells in unseparated mammalian blood, but are useful in a wide variety of other assays as well.

With respect to particle size, particles may simply be varied in diameter. Alternatively, particles could be assembled as doublets, triplets, or other higher-order multimers. Doublets and triplets often occur spontaneously in a population, and can be enriched for by fractionation.

With respect to surface properties, in one embodiment, the invention provides the use of metallization. This can dramatically alter the scattering properties of a surface. One way to accomplish this is to attach gold particles (e.g. colloidal gold) to an affinity molecule, such as streptavidin or DNA, and then to bind the molecule at defined loadings to specific sites on the bead. For example, ten different loadings could give ten new codes. Together with 100 fluorescence codes, this would allow the recognition of ~1000 bead types in an array. Alternatively, metallization could be used for the assay readout, and fluorescence for the encoding.

With respect to magnetism, superparamagnetic beads could be deflected according to the amount of magnetism, and directed to different readout channels, i.e. this mechanism could be used as a "pre-sorter" prior to fluorescence readout. In one version, bead subpopulations could be localized to different regions of a reaction vessel (e.g. microtiter well) by the use of small magnets. Each sub-population could be released sequentially for analysis.

Although the previously described method involving additional detection channels finds use in planar bead arrays, it also finds particular use in liquid arrays. By "liquid arrays" is meant a collection of beads that are not spatially organized, but are typically encoded by fluorescence labeling and "decoded" by readout on a flow-cytometer or equivalent instrument. Assays are carried out in bulk in solution. Generally, liquid arrays are designed such that the assay result and decoding result are obtained essentially simultaneously. However, because only optical images are detected simultaneously, the number of codes that can be analyzed is limited. That is, there is a limit to the number of codes that can be used since the number of assay signals and encoding signals must be determined at different wavelengths at essentially the same time. However, by using additional detection channels as described above, the number of codes that can be analyzed is markedly increased.

This method finds particular use in analyzing the results of genomics based assays such as gene expression profiling, genotyping and SNP analysis. In such genomics based assays, it is frequently desirable to make hundreds to millions of measurements simultaneously. Thus, by increasing the number of codes that can be simultaneously detected, analysis of such assays is enhanced.

This invention provides methods of maximizing the information that is obtained from a single bead. That is, by providing ways of multiplexing assays on a single bead, multiple parameters can be simultaneously detected. That is, after a cycle of performing a particular assay, decoding and reading the assay results, the bead population is recovered. The detection molecules are removed from the bead and the cycle is repeated.

In a preferred embodiment, parity analysis is used during decoding to increase the robustness and accuracy of the system. By "parity analysis" is meant a decoding step wherein the signal of a particular element is analyzed across a plurality of decoding stages. That is, following at least one decoding step, but most preferably following multiple decoding steps, the signal of an array element across the decoding stages is analyzed. That is, the signal from a particular bead is evaluated across multiple stages. Although the analysis includes any parameter that can be obtained from the signals such as evaluating the total signal obtained across the stages, in a preferred embodiment, the parity of the signals across the stages is analyzed.

By "parity" is meant the digital or modular readout of signals, i.e. odd or even, when binary signals are used. As depicted in FIG. 7, the digit sum of the signals across a plurality of stages is translated into a parity determination. The parity determination is then useful in evaluating the decoding process. An example is illustrative. Codes are designed to have an odd number of a particular signal, for example a red signal, when viewed across all stages or decoding steps, or a pre-determined plurality of stages or decoding steps. The detection of an even number of red stages, provides an indication that an error has occurred at some point in decoding. When this result is obtained, the faulty code can either be discarded, or the analysis repeated.

In a preferred embodiment the invention includes introducing a "redundant stage" into the decoding system. By "redundant stage" is meant a stage that serves as a parity check. That is, following the decoding stages, an additional stage is included to analyze the parity. This analysis provides an indication of the competence or validity of the decoding. That is, when codes are designed with a pre-determined parity, the redundant stage is used to detect the parity of the signals obtained from the decoding step. That is, the redundant stage detects errors in parity because if there has been an error in decoding, the parity detected following the redundant stage will be different from the parity designed into the codes.

An example is illustrative. In the following illustration, array elements are decoded in two stages with two colors. This results in the detection of 4 ($2^2$) codes. The codes are designed to result in odd parity following the analysis with the redundant stage. That is, the code sequences can be made such that each code will contain an odd number of "red" colors (when viewed across all stages, or when viewed across the pre-determined number of stages). In the illustration below, only the stage where the "red" signal is detected is indicated.

| Code | Stage 1 | Stage 2 | Redundant Stage | Parity (number of "red" stages) |
|---|---|---|---|---|
| 1 | 0 | 0 | red | 1 (odd) |
| 2 | 0 | red | 0 | 1 (odd) |
| 3 | red | 0 | 0 | 1 (odd) |
| 4 | red | red | red | 3 (odd) |

However, if there is an error during decoding, this will be reflected as detecting a parity that is different from that designed into the codes. In the following illustration the same codes as above are used however, an error is detected. In this case if one detects an even number of "red" stages it can be inferred that there has been a decoding error.

| Code | Stage 1 | Stage 2 | Redundant Stage | Parity (number of "red" stages) |
|---|---|---|---|---|
| 1 | 0 | 0 | red | 1 (odd) |
| 2 | 0 | red | 0 | 1 (odd) |
| 3 | red | 0 | 0 | 1 (odd) |
| 4 | red | o (error) | red | 2 (even) |

Although in some embodiments, the parity is binary, i.e. odd or even, in other embodiments the parity is modular or based on numbers other than 2. That is, the parity can be based on detection of 3 or more signals. In a preferred embodiment, the signals are multiple colors. In a particularly preferred embodiment the colors are red, green and blue.

An example is illustrative. In the following illustration, codes are decoded in two steps with three colors. This results in the detection of $3^2$ (9) signals. In the illustration, red is indicated by 1, green is indicated by 2 and blue is indicated by 3. The parity is based on a modulus 3. By including a third stage as a redundant stage the parity can be checked as described above.

| Code | Stage 1 | Stage 2 | Redundant stage | Parity |
|---|---|---|---|---|
| 1 | 1 | 1 | 1 | 3 |
| 2 | 1 | 2 | 3 | 6 |
| 3 | 1 | 3 | 2 | 6 |
| 4 | 2 | 1 | 3 | 6 |
| 5 | 2 | 2 | 2 | 6 |
| 6 | 2 | 3 | 1 | 6 |
| 7 | 3 | 1 | 2 | 6 |
| 8 | 3 | 2 | 1 | 6 |
| 9 | 3 | 3 | 3 | 9 |

However, when there is a decoding error, the parity will be incorrect; in the illustration the parity readout is not divisible by 3.

| Code | Stage 1 | Stage 2 | Redundant stage | Parity |
|---|---|---|---|---|
| 1 | 1 | 1 | 1 | 3 |
| 2 | 1 | 2 | 3 | 6 |
| 3 | 1 | 3 | 2 | 6 |
| 4 | 2 | 1 | 3 | 6 |
| 5 | 2 | 2 | 2 | 6 |
| 6 | 2 | 3 | 1 | 6 |
| 7 | 3 | 1 | 2 | 6 |
| 8 | 3 | 2 | 1 | 6 |
| 9 | 3 | 2 (error) | 3 | 8 |

Thus, a redundant stage allows for the detection of errors on the array or in the signal obtained from an array.

Although described above for detecting errors on arrays, the method of using redundant stages is not limited to arrays. That is, the method finds use in detecting errors In a variety of systems that send, receive and/or interpret or analyze data such as communications systems including modems etc. In particular, the method of using the modular redundant stages allows for processing of signals of vastly increased complexity as compared to sending bits of data. That is, when using modular redundant stages, characters as opposed to bits, can be sent across modem lines in the communications field. The modular redundant stage is used to detect errors in the communication or processing of the signals.

In an additional embodiment a redundant channel is used during the decoding. By "redundant channel" is meant either the use of multiple filters to analyze a particular signal or repeated use of the same filter to analyze the signal, i.e., multiple signals from the same channel. Redundant channels find use as a source of a "back-up" signal of sorts for a particular array element. That is, when multiple images are obtained as a result of redundant channels, the likelihood of obtaining the correct signal increases. That is, when it is realized that one of the results for an element is compromised for some reason, the image obtained from the redundant channel is used instead. When the initial image is not compromised, the result from the redundant channel need not be used, although it may be used, for example as a way to confirm the initial signal.

An example is illustrative. During decoding, when it is apparent that one stage fails, for example as a result of mis-registration of a channel, the use of a redundant channel serves to rescue the decoding at that particular stage. Mis-registration can also be addressed as outlined in U.S. Ser. No. 09/636,387, filed Aug. 9, 2000, which is expressly incorporated herein by reference. As noted above, the redundant channel can either be an image separate filter to analyze the signal, or alternatively, it can be multiple images taken from the same filter.

In one embodiment, the number of redundant channels increases as the number of decoding stages increases. Because the investment in decoding increases as each decoding stage or step proceeds, it is important in this embodiment to ensure the competence of decoding at later decoding stages.

In a preferred embodiment, redundant systems are used to avoid the loss of information. It is appreciated that when "S" decoding steps (sometimes referred to herein as "stages") and "C" colors are used, the maximum number of distinct signals is $C^S$ (C raised to the "S"th power). In some instances, the corruption of a stage results in the loss of $C^S-(C-1)\times C^{(S-1)}$ codes. Depending on the values of C and S, the loss can be substantial. Accordingly, the present invention provides for methods of improving the robustness of the decoding system. That is the invention provides for a method of confirming the results of a decoding analysis or detecting errors in a decoding analysis during or after the decoding procedure. The method also decreases the number of false positive or false negative signals; similarly, the number of true positives and/or true negatives increases.

In a preferred embodiment, several levels of redundancy are built into the arrays of the invention. Building redundancy into an array gives several significant advantages, including the ability to make quantitative estimates of confidence about the data and significant increases in sensitivity. Thus, preferred embodiments utilize array redundancy. As will be appreciated by those in the art, there are at least two types of redundancy that can be built into an array: the use of multiple identical sensor elements (termed herein "sensor redundancy"), and the use of multiple sensor elements directed to the same target analyte, but comprising different chemical functionalities (termed herein "target redundancy"). For example, for the detection of nucleic acids, sensor redundancy utilizes of a plurality of sensor elements such as beads comprising identical binding ligands such as probes. Target redundancy utilizes sensor elements with different probes to the same target: one probe may span the first 25 bases of the target, a second probe may span the second 25 bases of the target, etc. By building in either or both of these types of redundancy into an array, significant benefits are obtained. For example, a variety of statistical mathematical analyses may be done.

In addition, while this is generally described herein for bead arrays, as will be appreciated by those in the art, this techniques can be used for any type of arrays designed to detect target analytes.

In a preferred embodiment, sensor redundancy is used. In this embodiment, a plurality of sensor elements. e.g. beads, comprising identical bioactive agents are used. That is, each subpopulation comprises a plurality of beads comprising identical bioactive agents (e.g. binding ligands). By using a number of identical sensor elements for a given array, the optical signal from each sensor element can be combined and any number of statistical analyses run, as outlined below. This can be done for a variety of reasons. For example, in time varying measurements, redundancy can significantly reduce the noise in the system. For non-time based measurements, redundancy can significantly increase the confidence of the data.

In a preferred embodiment, a plurality of identical sensor elements are used. As will be appreciated by those in the art, the number of identical sensor elements will vary with the application and use of the sensor array. In general, anywhere from 2 to thousands may be used, with from 2 to 100 being preferred, 2 to 50 being particularly preferred and from 5 to 20 being especially preferred. In general, preliminary results indicate that roughly 10 beads gives a sufficient advantage, although for some applications, more identical sensor elements can be used.

Once obtained, the optical response signals from a plurality of sensor beads within each bead subpopulation can be manipulated and analyzed in a wide variety of ways, including baseline adjustment, averaging, standard deviation analysis, distribution and cluster analysis, confidence interval analysis, mean testing, etc.

In a preferred embodiment, the first manipulation of the optical response signals is an optional baseline adjustment In a typical procedure, the standardized optical responses are adjusted to start at a value of 0.0 by subtracting the integer 1.0 from all data points. Doing this allows the baseline-loop data to remain at zero even when summed together and the random response signal noise is canceled out When the sample is a fluid, the fluid pulse-loop temporal region, however, frequently exhibits a characteristic change in response, either positive, negative or neutral, prior to the sample pulse and often requires a baseline adjustment to overcome noise associated with drift in the first few data points due to charge buildup in the CCD camera. If no drift is present, typically the baseline from the first data point for each bead sensor is subtracted from all the response data for the same bead. If drift is observed, the average baseline from the first ten data points for each bead sensor is subtracted from the all the response data for the same bead. By applying this baseline adjustment, when multiple bead responses are added together they can be amplified while the baseline remains at zero. Since all beads respond at the same time to the sample (e.g. the sample pulse), they all see the pulse at the exact same time and there is no registering or adjusting needed for overlaying their responses. In addition, other types of baseline adjustment may be done, depending on the requirements and output of the system used.

Once the baseline has been adjusted, a number of possible statistical analyses may be run to generate known statistical parameters. Analyses based on redundancy are known and generally described in texts such as Freund and Walpole, Mathematical Statistics, Prentice Hall, Inc. New Jersey, 1980, hereby incorporated by reference in its entirety.

In a preferred embodiment, signal summing is done by simply adding the intensity values of all responses at each time point, generating a new temporal response comprised of the sum of all bead responses. These values can be baseline-adjusted or raw. As for all the analyses described herein, signal summing can be performed in real time or during post-data acquisition data reduction and analysis. In one embodiment, signal summing is performed with a commercial spreadsheet program (Excel, Microsoft, Redmond, Wash.) after optical response data is collected.

In a preferred embodiment, cumulative response data is generated by simply adding all data points in successive time intervals. This final column, comprised of the sum of all data points at a particular time interval, may then be compared or plotted with the individual bead responses to determine the extent of signal enhancement or improved signal-to-noise ratios.

In a preferred embodiment, the mean of the subpopulation (i.e. the plurality of identical beads) is determined, using the well known Equation 1:

$$\mu = \sum \frac{x_t}{n} \qquad \text{Equation 1}$$

In some embodiments, the subpopulation may be redefined to exclude some beads if necessary (for example for obvious outliers, as discussed below).

In a preferred embodiment, the standard deviation of the subpopulation can be determined, generally using Equation 2 (for the entire subpopulation) and Equation 3 (for less than the entire subpopulation):

$$\sigma = \sqrt{\frac{\sum (x_i - \mu)^2}{n}} \qquad \text{Equation 2}$$

$$s = \sqrt{\frac{\sum (x_i - \bar{x})^2}{n-1}} \qquad \text{Equation 3}$$

As for the mean, the subpopulation may be redefined to exclude some beads if necessary (for example for obvious outliers, as discussed below).

In a preferred embodiment, statistical analyses are done to evaluate whether a particular data point has statistical validity within a subpopulation by using techniques including, but not limited to, t distribution and cluster analysis. This may be done to statistically discard outliers that may otherwise skew the result and increase the signal-to-noise ratio of any particular experiment. This may be done using Equation 4:

$$t = \frac{\bar{x} - \mu}{s / \sqrt{n}} \qquad \text{Equation 4}$$

In a preferred embodiment, the quality of the data is evaluated using confidence intervals, as is known in the art. Confidence intervals can be used to facilitate more comprehensive data processing to measure the statistical validity of a result.

In a preferred embodiment, statistical parameters of a subpopulation of beads are used to do hypothesis testing. One application is tests concerning means, also called mean testing. In this application, statistical evaluation is done to determine whether two subpopulations are different. For example, one sample could be compared with another sample for each subpopulation within an array to determine if the variation is statistically significant.

In addition, mean testing can also be used to differentiate two different assays that share the same code. If the two assays give results that are statistically distinct from each other, then the subpopulations that share a common code can be distinguished from each other on the basis of the assay and the mean test, shown below in Equation 5:

$$z = \frac{\bar{x}_1 - \bar{x}_2}{\sqrt{\frac{\sigma_1^2}{n_1} + \frac{\sigma_2^2}{n_2}}} \qquad \text{Equation 5}$$

Furthermore, analyzing the distribution of individual members of a subpopulation of sensor elements may be done. For example, a sub population distribution can be evaluated to determine whether the distribution is binomial, Poisson, hypergeometric, etc.

In addition to the sensor redundancy, a preferred embodiment utilizes a plurality of sensor elements that are directed to a single target analyte but yet are not identical. For example, a single target nucleic acid analyte may have two or more sensor elements each comprising a different probe. This adds a level of confidence as non-specific binding interactions can be statistically minimized. When nucleic acid target analytes are to be evaluated, the redundant nucleic acid probes may be overlapping, adjacent, or spatially separated. However, it is preferred that two probes do not compete for a single binding site, so adjacent or separated probes are preferred. Similarly, when proteinaceous target analytes are to be evaluated, preferred embodiments utilize bioactive agent binding agents that bind to different parts of the target. For example, when antibodies (or antibody fragments) are used as bioactive agents for the binding of target proteins, preferred embodiments utilize antibodies to different epitopes.

In this embodiment, a plurality of different sensor elements may be used, with from about 2 to about 20 being preferred, and from about 2 to about 10 being especially preferred, and from 2 to about 5 being particularly preferred, including 2, 3, 4 or 5. However, as above, more may also be used, depending on the application.

As above, any number of statistical analyses may be run on the data from target redundant sensors.

One benefit of the sensor element summing (referred to herein as "bead summing" when beads are used), is the increase in sensitivity that can occur.

Once made, the compositions of the invention find use in a number of applications. In a preferred embodiment, the compositions are used to probe a sample solution for the presence or absence of a target analyte, including the quantification of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications. Such applications are described in more detail in U.S. Ser. Nos. 60/130,089, filed Apr. 20, 1999; 60/160,927, filed Oct. 22, 1999; 09/513,362, filed Feb. 25, 2000; 60/135,051, filed May 20, 1999; 60/161,148, filed Oct. 22, 1999; 09/517,945, filed Mar. 3, 2000; 09/425,633, filed Oct. 22, 1999; 09/535,854, filed Mar. 27, 2000; 09/535,993, filed Apr. 20, 2000; 09/556,463, filed Apr. 21, 2000; 60/224,119, filed Oct. 26, 2000, all of which are expressly incorporated herein by reference.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences, as is described in more detail in U.S. Ser. No. 09/425,633, filed Oct. 22, 1999, Ser. No. 09/535,854, filed Mar. 27, 2000, both of which are expressly incorporated herein by reference. For example, recent focus has been on the analysis of the relationship between genetic variation and phenotype by making use of polymorphic DNA markers.

Previous work utilized short tandem repeats (STRs) as polymorphic positional markers; however, recent focus is on the use of single nucleotide polymorphisms (SNPs). Common SNPs occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor, et al., *Science* 261 (1993). Multiplex PCR amplification of SNP loci with subsequent hybridization to oligonucleotide arrays has been shown to be an accurate and reliable method of simultaneously genotyping at least hundreds of SNPs; see Wang, et al., *Science,* 280:1077 (1998); see also Schafer, et al., *Nature Biotechnology* 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$, with less than about $10^{-5}$ to $10^{9}$ $M^{-1}$ being preferred and less than about $10^{-7}$-$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optically interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorochromes, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optically detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

The assays may be run under a variety of experimental conditions, as will be appreciated by those in the art. A variety of other reagents may be included in the screening assays. These include reagents like salts, neutral proteins, e.g. albumin, detergents, etc. which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophor, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs. The 3' end of the primer is located adjacent to the SNP site. In this way, the single base extension is complementary to the sequence at the SNP site. By using four different fluorophors, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased specificity which is particularly helpful for the analysis of complex samples.

In addition, when the target analyte and the DBL both bind to the agent, it is also possible to do detection of non-labeled target analytes via competition of decoding.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal-this can be detected during decoding. The omission of one or more agents from multiple arrays can also be detected; that is, since the arrays formulated herein are randomly self-assembled, arrays comprising different statistical distributions of each sensor elements may be made; the invention allows actual QC on the arrays, for "sorting" arrays with good distributions from those with less than ideal distributions. These procedures also allow the determination of sites that do not comprise beads. This quality control procedure can also be used in non-random arrays.

An advantage of this quality control procedure is that it can be implemented immediately prior to the assay itself (or after, in some instances), and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In an alternative method of quality control, a single fiber bundle of an array is dedicated to quality control. That is a dedicated bundle or subset of fibers within an array is independently analyzed for quality control. In one embodiment, the control fiber(s) are targeted or labeled with a unique code or label. At each state of hybridization, in addition to the experimental probes, the quality control probes are hybridized with the array. Upon taking the image from the first hybridization of the first stage, the intensity of the control fiber(s) is analyzed. An aberrant reading or signal from the control fiber indicates a failed or at least non-optimal hybridization step.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. For example, when large populations of different random oligonucleotides are synthesized, it may be desirable to check that each population is represented. The approach described here can be used to do this by treating the reagents (formulated as the DBLs) as variable Instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. For example, different probes can show differences in hybridization efficiencies, etc., and it may be desirable to choose appropriate probes under experimental conditions. Thus, for example, when expression profiling is done, and quantitation is desirable, calibration curves can be done to see how individual probes react, and then the probes that give the best response (i.e. linearity at the concentrations and conditions of interest) can be chosen for further assays. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array.

Thus, in these embodiments, different types of experiments can be done. For example, the sequential decoding scheme can be implemented with different concentrations being used as the code "labels", rather than different fluorophores. In this way, signal as a response to concentration can be measured for each bead. This calibration can be carried out just prior to array use, so that every probe on every array is individually calibrated as needed. Alternatively, different concentrations of the decoding probe can have different labels.

It should be noted that the assay calibration methods find use in non-random arrays, as well; that is, other types of support-bound nucleic acid arrays can be calibrated using these methods as well. Thus, for example, the sequential addition of different pools of probes, wherein the concentration of the probes is varied, to biochips can allow calibration of any assay system. This type of analysis can also be done on non-random arrays for quality control, to verify the integrity and sequence of the support bound probes, and in assay development to identify good probes.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development. Thus, probes that respond linearly with concentration, show low nonspecific binding, or give signals in a particular range, can be chosen for addition to a new array for assays.

Similarly, in a preferred embodiment, the methods of the invention are useful in quantitation in assay development. Major challenges of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, that can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are selected empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

In a preferred embodiment, cDNA arrays are made for RNA expression profiling. In this embodiment, individual cDNA clones are amplified (for example, using PCR) from cDNA libraries propagated in a host-vector system. Each amplified DNA is attached to a population of beads. Different populations are mixed together, to create a collection of beads representing the cDNA library. The beads are arrayed, decoded as outlined above, and used in an assay (although as outlined herein, decoding may occur after assay as well). The assay is done using RNA samples (whole cell or mRNA) that are extracted, labeled if necessary, and hybridized to the array. Comparative analysis allows the detection of differences in the expression levels of individual RNAs. Comparison to an appropriate set of calibration standards allows quantification of absolute amounts of RNA.

The cDNA array can also be used for mapping, e.g. to map deletions/insertions or copy number changes in the genome, for example from tumors or other tissue samples. This can be done by hybridizing genomic DNA. Instead of cDNAs (or ESTs, etc.), other STS (sequence tagged sites), including random genomic fragments, can also be arrayed for this purpose.

In one embodiment, the invention provides a method of single nucleotide polymorphism (SNP) genotyping. As described herein and in U.S. Ser. Nos. 09/553,993 filed Apr. 20, 2000, 09/556,463 filed Apr. 21, 2000 and 60/244,119, filed Oct. 26, 2000, all of which are expressly incorporated herein by reference, a target nucleic acid is contacted with a probe that is specific for a particular allele of a single nucleotide polymorphism. The target nucleic acid can be immobilized prior to contacting with the probe, or alternatively, the probe: target hybridization can occur in solution following by immobilization of the probe: target nucleic acid complex. Alternatively, a capture prove on a bead may be specific for a particular SNP. What is important in this invention is the nature of the probe for detecting a SNP.

There are four possibilities for the bases at a polymorphic site: -A, T, G, or C. However, it is known that most of the human SNP's are dimorphic, i.e., they only include the combinations of two of the four bases. As such, the prior art generally relied on distinguishing between two alleles that are present within a SNP. and characterized them as either "AA", "AB", or "BB".

However, according to the present invention, the probes are designed such that each of the four possible nucleotides that could be present at a particular position are included in the SNP probes. In addition, the probes are labeled with a specific color that corresponds with the nucleotide that hybridizes to the nucleotide to be interrogated. For instance, all the alleles that correspond to an A-polymorphic site are labeled with red. Similarly, all the alleles that correspond to a G-polymorphic site are labeled green, etc. As such the true identity of the polymorphism is determined. That is, if the polymorphism is of the type GT, one would not classify is as "AB" genotype. Instead, the GT code will come up directly from the genotyping routine.

An advantage of this method over the prior art is the capability of independent error checking. That is, knowing that polymorphisms are typically dimorphic, by using probes that correspond to all possibilities of polymorphisms at a sites, one obtains a check against false results, for example of a signal is detected that does not correspond with the known polymorphisms. That is, in the prior art, the resultant genotyping would be one of the following three possibilities: AA, AB, or BB. However, by using this invention, the number of possible results is increased from 3 to 10: AA, AG, AC, AT, GG, GC, GT, CC, CT, TT. Of these ten possibilities, only 3 are the possible combinations for each SNP, e.g., a T/G polymorphism can only render one of the following three possibilities: TT, TG, or GG. Therefore, in this case, if the computed genotype falls into any of the remaining 10–3=7 combinations (e.g., either of AA, AG, AC, AT, GC, CC, CT), it would be a clear indication that an error has occurred.

All references cited herein are incorporated by reference in their entirety.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Sixteen microspheres (beads) were labeled combinatorially with two different fluorophores (FAM and Cy3). In a first round of labeling, either FAM or Cy3-labeled oligonucleotides that were complementary to the oligonucleotide (IBL) on the microsphere, were hybridized with the microsphere. Labeling of oligonucleotides was performed as is well known in the art. Hybridization conditions are known in the art.

Following a first round of hybridization, the two pools of beads were divided into two pools each and each labeled either with the FAM or Cy3-labeled oligonucleotide. This process was repeated two additional times. Thus, following four successive rounds of labeling, each microsphere was labeled with a unique code (see FIG. 1). The identity of each microsphere was elucidated by determining the identity of each fluorophore in succession; the terminal fluorophore was determined and then removed to allow for the identification of the next fluorophore. In this fashion, with as few as 4 decoding steps, the identity of 16 microspheres is determined.

Example 2

A decoding scheme similar to that described in Example 1 was implemented for four color decoding. In this example, beads were labeled as described in Example 1 with the exception that 4 labels were used at each stage. 4013 beads were labeled using Bod493, BodR6G, Bod564 and BodTXR labeled oligonucleotides. 128 different bead types were identified based on the successive decoding of the four colors.

Example 3

An alternative method to using multiple colors is to use ratiometric intensities as a coding scheme. A normalizing image is acquired in which every bead exhibits its "full" intensity. Subsequent decode stages generate intensity codes by hybridizing mixtures of "labeled":"unlabeled" complementary oligonucleotides. For instance, FIG. 1 depicts three different intensity shades (low, medium, and high) which can be ratioed to a stage with all complements present at a "high" shading value. An experiment using grey scale decoding on 16 different bead types is shown in FIG. 3.

FIG. 3A depicts the combinatorial pooling scheme for labeling beads with different ratios of labeled oligonucleotides. A particular oligo is present at either 100% Cy3-labeled, 40% Cy3-labeled (60% unlabeled), or 10% Cy3-labeled (90% unlabeled) fraction. Decode oligos were hybridized to the array for 2 min. at a 50 nM concentration. Subsequently, two independent normalizing images (all oligo complements are present as 100% Cy3-labeled species) were acquired, and the resulting bead intensities compared. This is depicted in FIG. 3B as the normalized values are plotted against each other. Finally, to identify or decode the beads, the alpha values (ratio of bead intensity in indicated decode stage to intensity in normalization image) are plotted for three decode stages described in (A). In stage 1, only two peaks are observed in the alpha value histogram since only 16 bead types are present on the array. Three distinguishable peaks are observed in the second and third decode stages indicating the feasibility of grey scale decoding.

Physical attributes and different "levels" of the attributes can be used as codes by which to distinguish bead types from another. Thus, for an attribute to act as a robust code, it should be possible to imbue a bead with different "levels" of a particular attribute. Each "level" of an attribute should be quantitatively well separated from other "levels". The important point is to maximize the dynamic range of the attribute measurement, and minimize the spread of the measurement.

Example 4

For a given oligo sequence, several codes can be generated by varying the distance of separation of the two fluorophores. As shown in FIG. 4, a complementary sequence containing FRET dyes separated by a linker of varying lengths allows multiple codes to be generated (FIG. 4A). As an example, Probe A and B are hybridized to a complementary sequence immobilized on a solid support. Probe A contains dyes separated by an 8 poly T linker, whereas probe B is hybridized to a linker with a 4 poly T linker. The efficiency of energy transfer (ratio of intensities of dye2:dye1) is greater for probe B than for probe A (FIG. 4B).

Example 5

The following FRET oligonucleotides (probes ET1, ET2, ET5 and ET7) were synthesized as is known in the art and labeled with Cy3 and fluorscein separated by linkers of varying length:

```
ET1
                                         (SEQ ID NO: 1)
T**G*CACGAGAATGGAGGTATCT

ET2
                                         (SEQ ID NO: 2)
C**TGTCGC*ACGAGAATGGAGGTATCT

ET5
                                         (SEQ ID NO: 5)
C**TGTCGGGGCACTCATTTGTGC*ACGAGAATGGAGGTATCT

ET7
                                         (SEQ ID NO: 6)
C**TGTCGGGGCACTCATTTGTCTGTCGGGCGC*ACGAGAATGGAGGTA
TCT.

** is Cy3

* is fluorescein
```

An aliquot of each FRET oligonucleotide was assayed as is known in the art. Emission spectra were normalized relative to emission at 530 nm. As can be seen in FIG. 5 emission of fluorescein increases as the linker is shortened. The ratio of intensities of the two fluorophores, therefore, is characteristic of the distance between the fluorophores.

Example 6

To illustrate the primer extension decoding, a two-color model is illustrated in FIG. 9. To decode 16 different bead addresses using only two colors. 16 different beads are labeled by attaching 16 different unique oligos (IBLs) to each of 16 batches of beads and pooling the bead batches together. Along with the beads 16 oligos (DBLs) that are complementary to these IBLs are synthesized. Each unique IBL used in this method contains two domains. The domains are composed of a binding domain and an extension domain. The pooled bead populations are then self-assembled onto a fiber optic tip end as described herein. After array self-assembly a combinatorial color decoding process is initiated as follows: A primer extension reaction is initiated at the end of the fiber bundle tip containing the arrayed beads by simultaneously hybridizing 16 complementary oligos (DBLs) to their cognate IBL. In the first extension stage, the DBLs would have exactly the same length (n) as the binding domain of the IBL. The first stage primer extension reaction would contain 16 primer oligos, a DNA polymerase, appropriate buffer, and two fluorescently-labeled dideoxynucleotide terminators. During the extension reaction, hybridized primers are extended by a single nucleotide complementary to the first nucleotide in the extension domain of the immobilized IBL. The described extension reaction "paints" or labels any given bead with one of two possible fluorescent terminator colors. After the reaction is over the array tip is imaged to capture the color of the beads at this stage. Beads are then immediately stripped of color or label by denaturing and washing off the first extended primer at each zip code loci. This process can be repeated through multiple stages. In subsequent stages, the primer extension reactions contain the same reagents as the previous extension reaction except that the binding complementary oligos are one base longer. These (n+1) primers hybridize with their cognate binding domain and one base into the "extension domain". FIG. 9 illustrates a four-stage extension process (2-color) whereby each stage allows for the assignment of a unique combinatorial color-coded 'address' to each bead type.

In addition, if this primer-based extension method were to be combined with degenerate DBL-BL combinations for decoding large combinatorial libraries, for example using the CVC (constant-variable-constant domain idea), as described herein, the extension reaction would extend into one of 10 different possible nucleotide combinations in a "variable extension region". This would require only three extension reactions to decodify 1000 unique addresses (i.e. A=lot where L is the length of the variable region). The combination of the degenerate DBL-IBL combinations such as CVC with the primer extension method is illustrated in FIG. 10.

Example 7

This method relates to fluorescent based encoding and decoding process based on the fact that fluorescent dyes have broad band absorption and emission spectra. Fewer detection channels are used than the number of encoding dyes used in the process. That is, for n detection channels, a particular dye, x, can be represented by a vector $I_x$ in the n-dimensional space.

$$I_x \left\{ \frac{1}{\sum_{i=1}^{n} f I_i} \right\} I_1 I_2 I_3 \ldots I_n$$

where $I_i$ is the intensity detected at channel i. Theoretically, an infinite number of vectors are possible in the n-dimensional space when n is larger or equal to 2. With an appropriate dye selection and optical filter design, for any given number of detection channels, a larger number of dyes can be used for decoding. For example, to distinguish three species, it is possible to tag the species with three different dyes, x, y, z and use only two detection channels, such that $$I_x = \{1\ 0\}$$

$$I_y = \{a\ 1-a\}\ 0<a<1$$

$$I_z = \{0\ 1\}$$

FIG. 11 illustrates the experimental results for this example scheme used in decoding. Three classes of beads were tagged with Bodipy-493, Bodipy-R6G and Bodipy564. Detection channel 1 consisted of a 410 nm/20 excitation filter and a 540 nm/20 emission filter. Detection channel 2 consisted of a 535 nm/20 excitation filter and a 585 nm/nm emission filter. Excited with a xenon arc lamp, the fluorescence emission of Bodipy-493 can only be detected in channel 1. Bodipy-564 emission can be detected in channel 2. Bodipy-R6G can be detected in both channels. As expected, the scatter plot (FIG. 11) of the intensity in the two channels of the beads clearly indicates three classes. Within each class, the beads have the same relative intensity ratio (corresponding to the same unit vector) with a certain uncertainties.

Similar design and data analysis procedure can be used for other dyes and detection channels.

What is claimed is:

1. A method of decoding an array, said method comprising:
   a) providing an array comprising a plurality of bioactive agents randomly distributed at sites of said array, wherein each of a plurality of said sites further comprises at least a first and a second identifier binding ligand (IBL);
   b) detecting binding of a first decoder binding ligand (DBL) to the first IBL;
   c) detecting binding of a second DBL to the second IBL; and
   d) determining the location of the first and second IBLs, thereby decoding the position of one or more bioactive agents on said array; and
   wherein said first IBL and said second IBL each comprise different nucleic acid sequences.

2. The method of claim 1, wherein said array comprises glass or plastic.

3. The method of claim 1, wherein said array comprises a fiber optic bundle.

4. The method of claim 1, wherein said array comprises a flat planar surface.

5. The method of claim 4, wherein said flat planar surface comprises one or more depressions.

6. The method of claim 1, wherein said plurality of bioactive agents and said first and second IBLs each comprise a nucleic acid.

7. The method of claim 6, wherein said nucleic acid is selected from the group consisting of DNA and RNA.

8. The method of claim 6, wherein said nucleic acid is single-stranded.

9. The method of claim 6, wherein said one of said first and second IBLs comprises substantially the same nucleic acid sequence as one or more bioactive agents.

10. The method of claim 1, wherein said sites of are divided into a first and a second subpopulation of sites, and wherein said first and second IBLs are attached to said first subpopulation of sites at a first ratio and are attached to said second subpopulation of sites at a second ratio.

11. The method of claim 6, wherein said nucleic acid is an oligonucleotide of about 8 to about 40 nucleotides in length.

12. The method of claim 1, wherein said DBL comprises a fluorophore.

13. The method of claim 1, wherein said sites are regularly arrayed on said array.

14. The method of claim 13, wherein said regularly arrayed sites are addressable in an X-Y format.

15. The method of claim 1, wherein said sites are depressions.

16. The method of claim 15, wherein said depressions are wells.

17. The method of claim 1, wherein step a) comprises randomly distributing said bioactive agents to an array substrate comprising an etched surface having sites.

18. The method of claim 17, wherein said sites are wells.

19. The method of claim 6, wherein said first and second IBLs each comprise a different nucleic acid sequence from said bioactive agents.

20. A method of decoding an array comprising:
   a) providing an array comprising a population of microspheres randomly distributed at sites of said array, wherein each microsphere is associated with a bioactive agent, a first identifier binding ligand (IBL), and a second IBL, and wherein said first IBL and said second IBL each comprise a different nucleic acid sequence;
   b) detecting binding of a first decoder binding ligand (DBL) to the first IBL;
   c) detecting binding of a second DBL to the second IBL; and
   d) determining the site having the microsphere comprising the first and second IBLs, thereby decoding the position of one or more bioactive agents on said array.

21. The method of claim 20, wherein said bioactive agent comprises a nucleic acid that is substantially the same as the first IBL.

22. The method of claim 20, wherein the bioactive agent comprises a nucleic acid that is different from the first IBL and the second IBL.

23. The method of claim 20, wherein the array comprises an etched surface.

* * * * *

UNITED STATES PATENT AND TRADEMARK OFFICE
CERTIFICATE OF CORRECTION

PATENT NO. : 8,460,865 B2
APPLICATION NO. : 11/739668
DATED : June 11, 2013
INVENTOR(S) : Mark S. Chee et al.

It is certified that error appears in the above-identified patent and that said Letters Patent is hereby corrected as shown below:

Title Page 4, Col. 2, Line 23, Under Other Publications, change "byOligonucleotide" to --by Oligonucleotide--.

Title Page 4, Col. 2, Line 58, Under Other Publications, change "Addressab le" to --Addressable--.

Title Page 5, Col. 2, Line 5, Under Other Publications, change "Monlayers" to --Monolayers--.

Title Page 5, Col. 2, Line 44, Under Other Publications, change "Eurpoean" to --European--.

Title Page 5, Col. 2, Line 51, Under Other Publications, change "Immobolized" to --Immobilized--.

Title Page 6, Col. 1, Line 35, Under Other Publications, change "Tiber" to --"Fiber--.

Title Page 6, Col. 1, Line 51, Under Other Publications, change "la.," to --al.,--.

Title Page 6, Col. 1, Line 52, Under Other Publications, change "TrtRahedron" to --TetRahedron--.

Title Page 6, Col. 2, Line 48, Under Other Publications, change "Proceecings" to --Proceedings--.

In the Drawings
At Sheet 12 of 13, Line 3, Figure 15, change "Exonnclease" to --Exonuclease--.

In the Specifications
At Column 7, Line 8, change "Photoactivatible" to --Photoactivatable--.
At Column 11, Line 62, change "thereof" to --thereof.--.
At Column 12, Lines 30-31, change "procaryotic" to --prokaryotic--.
At Column 13, Lines 33-34, change "methylphophoroamidite" to --methylphosphoramidite--.
At Column 13, Line 50, change "Biorganic" to --Bioorganic--.
At Column 13, Line 52, change "3 7:473" to --37:473--.
At Column 15, Line 1, change "procaryotic" to --prokaryotic--.
At Column 22, Line 6, change "Photoactivatible" to --Photoactivatable--.

Signed and Sealed this
Twelfth Day of November, 2013

Teresa Stanek Rea
*Deputy Director of the United States Patent and Trademark Office*

CERTIFICATE OF CORRECTION (continued)
U.S. Pat. No. 8,460,865 B2

At Column 22, Line 7, change "Photoactivatible" to --Photoactivatable--.

At Column 24, Line 3, change "Malacite" to --Malachite--.

At Column 27, Line 25, change "0,1" to --0,0,1--.

At Column 28, Line 1, change "olligos" to --oligos--.

At Column 28, Line 4, change "olligos" to --oligos--.

At Column 43, Line 52, change "damaged" to --imaged--.

At Column 46, Line 22, change "flourophores" to --fluorophores--.

At Column 49, Line 11, change "cutoff" to --cutoff.--.

At Column 56, Line 65, change "procaryotic" to --prokaryotic--.

At Column 59, Line 48, change "fluorophor," to --fluorophore,--.

At Column 60, Line 1, change "fluorophors," to --fluorophores,--.

At Column 63, Line 66, change "fluorophere" to --fluorophore--.

At Column 65, Line 9, change "fluorscein" to --fluorescein--.

In the Claims

At Column 69, Line 35, in Claim 10, before "are" delete "of".